(12) United States Patent
Warren et al.

(10) Patent No.: US 6,258,781 B1
(45) Date of Patent: *Jul. 10, 2001

(54) PEPTIDE SPECIFICITY OF ANTI-MYELIN BASIC PROTEIN AND THE ADMINISTRATION OF MYELIN BASIC PROTEIN PEPTIDES TO MULTIPLE SCLEROSIS PATIENTS

(75) Inventors: Kenneth G. Warren; Ingrid Catz, both of Edmonton (CA)

(73) Assignee: The Governors of The University of Alberta (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/007,520

(22) Filed: Jan. 15, 1998

Related U.S. Application Data

(63) Continuation of application No. 08/327,357, filed on Oct. 21, 1994, now Pat. No. 5,817,629, which is a continuation-in-part of application No. 07/798,099, filed on Nov. 27, 1991, now abandoned.

(30) Foreign Application Priority Data

Oct. 22, 1991 (CA) ................................ 2053799-0

(51) Int. Cl.[7] .............................. A61K 38/00; C07K 5/00; C07K 7/00
(52) U.S. Cl. ................................ 514/13; 514/12; 514/14; 514/15; 514/16; 530/300; 530/326; 530/327; 530/328; 530/329
(58) Field of Search ................................ 514/12, 13, 14, 514/15, 16; 530/300, 326, 327, 328, 329

(56) References Cited

U.S. PATENT DOCUMENTS

| | | | |
|---|---|---|---|
| 5,571,499 | 11/1996 | Hafler et al. | 414/43 |
| 5,571,500 | 11/1996 | Hafler et al. | 424/43 |
| 5,641,474 | 6/1997 | Hafler et al. | 424/43 |
| 5,645,820 | 7/1997 | Hafler et al. | 424/41 |
| 5,858,364 | 1/1999 | Weiner et al. | 424/184.1 |
| 5,858,980 | 1/1999 | Weiner et al. | 514/13 |
| 5,869,054 | 2/1999 | Weiner et al. | 424/184.1 |
| 5,869,093 | 2/1999 | Weiner et al. | 424/451 |
| 5,935,577 | 8/1999 | Weiner et al. | 424/184.1 |
| 5,948,764 | 9/1999 | Gaur et al. | 514/14 |
| 6,036,957 | 3/2000 | Weiner et al. | 424/184.1 |
| 6,039,947 | 3/2000 | Weiner et al. | 424/184.1 |

FOREIGN PATENT DOCUMENTS

| | | |
|---|---|---|
| 0304279 | 2/1989 | (EP) . |
| 8810120 | 12/1988 | (WO) . |
| 9115225 | 10/1991 | (WO) . |
| 9308212 | * 4/1993 | (WO) ............................ C07K/13/00 |
| 9321222 | * 10/1993 | (WO) ............................ C07K/7/08 |

OTHER PUBLICATIONS

"Preparation and Properties of Monoclonal Antibodies to Myelin Baasic Protein and its Peptides," Nigel Groome et al., Neurochem. Int., vol. 7, No. 2, 1985, pp. 309–317.

"Monoclonal Antibodies Reactive with Myelin Basic Protein," Sarka Hruby et al., Molecular Immunoogy, vol. 24, No. 12, 1987, pp. 1359–1364.

"Characterization of Myelin Basic Protein Catabolism Products in the Cerebrospinal Fluid from Multiple Sclerosis Stroke and Head Injury Patients," Richard Barry et al., Neurochem. Int., vol. 18, No. 2, 1991, pp. 291–300.

"T–cell recognition of an immunodominant myelin basic protein epitope in multiple sclerosis," Kohei Ota et al., Nature, vol. 346, (1990), pp. 183–187.

"Peptides of myelin basic protein stimulate T lymphocytes from patients with multiple sclerosis," Constantin N. Baxevanis et al., Journal of Neuroimmunology, 22 (1989), pp. 23–30.

"A Myelin Basic Protein Peptide Is Recognized by Cytotoxic T Cells in the Context of Four HLA–DR Types Associated with Multiple Sclerosis," Roland Martin et al., The Journal of Experimental Medicine, vol. 173, Jan. 1991, pp. 19–24.

"Suppression and Reversal of Allergic Encephalomyelitis in Rhesus Monkeys with Basic Protein and Peptides," E.H. Eylar et al., Neurochemical Research (4), 1979, pp. 249–258.

(List continued on next page.)

Primary Examiner—Avis M. Davenport
(74) Attorney, Agent, or Firm—Fish & Richardson P.C.

(57) ABSTRACT

Human myelin basic protein (h-MBP) has a molecular weight of 18.5 KD and contains 170 amino acid residues. Synthetic peptides ranging in length from about 8 to 25 residues and covering the entire length of the protein have been produced. Antibodies to h-MBP (anti-MBP) were found to be neutralized by the synthetic peptides, in vitro, which span the h-MBP from about amino acid residue 61 to about amino acid residue 106. The peptides, which cover both the amino (about residues 1 to 63) and carboxy (about residues 117 to 162) terminals of h-MBP did not neutralize purified anti-MBP. Intrathecal administration of peptide MBP75–95, either as a single dose, or as repeated injections for periods up to 10 weeks, produced complete binding-neutralization of free (F) anti-MBP with no change in bound (B) levels. A control peptide MBP35–58 had no effect on F or B anti-MBP levels. Intravenous administration of MBP75–95 resulted in significant decline of F and B CSF anti-MBP levels over a period of one month. Administration of MBP synthetic peptides to MS patients either intrathecally or intravenously did not have any adverse neurological effects and systemic complications did not occur. The MBP epitope for MS anti-MBP has been localized to an area between Pro85 and Pro96.

10 Claims, 13 Drawing Sheets

OTHER PUBLICATIONS

"Fine Specificity and HLA Restriction of Myelin Basic Protein Specific Cytotoxic T Cell Lines from Multiple Sclerosis Patients and Healthy Individuals," Roland Martin et al., The Journal of Immunology, vol. 145, Jul. 15, 1990, pp. 540–548.

"Response of Human T Lymphocyte Lines to Myelin Basic Protein: Association of Dominant Epitopes with HLA Class II Restriction Molecules," Yuan K. Chou et al., Journal of Neuroscience Research 23, 1989, pp. 207–216.

"Prevention of experimental encephalomyelitis with peptides that block interaction of T cells with major histocompatibility complex proteins," Koichiro Sakai et al., Proc. Natl. Acad. Sci. USA, vol. 86, Dec. 1989, pp. 9470–9474.

Barry et al., *Neurochem. Int.,* vol. 18, No. 2, pp. 291–300, 1991.*

* cited by examiner

PEPTIDE SPECIFICITY OF ANTI-MYELIN BASIC PROTEIN AND THE ADMINISTRATION OF MYELIN BASIC PROTEIN PEPTIDES TO MULTIPLE SCLEROSIS PATIENTS

This application is a continuation of application Ser. No. 08/327,357, filed Oct. 21, 1994 now U.S. Pat. No. 5,817,629 which is a continuation-in-part of application Ser. No. 07/798,099, field Nov. 27, 1991, now abandoned.

FIELD OF INVENTION

This invention is concerned with selected polypeptides and their use in the immunoregulation of antibodies to human myelin basic protein. This invention also relates to novel pharmaceutical compositions containing these selected polypeptides and to a method of using these peptides for the treatment of Multiple Sclerosis.

BACKGROUND AND PRIOR ART

Multiple sclerosis (MS) is a multifocal demyelinating disease of the human central nervous system (CNS) associated with inflammation. Increased intra-blood-brain barrier (intra-BBB) IgG synthesis is a hallmark of MS (Tourtelotte, W. W., J Neurol Sci 10: 279–304, 1970; Link, H. and Tibbling, G., Scand J Clin Lab Invest 37: 397–401, 1977; Tourtelotte, W. W. and Ma, B., Neurology 28: 76–83, 1978; Walsh, J. M. and Tourtelotte, W. W., In: Hallpike, J. F., Adams, C. W. M. and Tourtelotte, W. W., eds. Multiple sclerosis. Baltimore. Williams & Wilkins, 1982: 275–358; and Warren, K. G., and Catz, I. Ann Neurol 17: 475–480, 1985).

IgG synthesis within the BBB is generally elevated in clinically definite MS patients (Schumacher, G. A., Beebe, G., Kibler R. E., et al., Ann N.Y. Acad Sci 15:266–272, 1965) with active or inactive disease. The specificity of the majority of the CNS IgG is unknown. While a small proportion has antiviral activity or reacts against brain antigens, nucleic acids, erythrocytes or smooth muscle antigens, the nonspecific portion may represent polyclonal activation of B-cells (Tourtelotte, W. W., and Ma, B., Neurology 28:76–83, 1978). During the last decade there has been considerable interest in the study of antibodies to specific myelin proteins.

Following the detection of circulating immune complexes containing myelin basic protein (MBP) as their antigenic component (Dasgupta, M. K, Catz, I, Warren, K. G. et al., Can J Neurol Sci 10:239–243, 1983), increased titers of antibodies to MBP (anti-MBP) were observed in the cerebrospinal fluid (CSF) of patients with active forms of MS (Warren, K. G. and Catz, I., Ann Neurol 209:20–25, 1986). Clinically, MS is characterized by phases of disease activity such as acute relapses or chronic progression, and by phases of clinical remission. Active MS is associated with increased levels of intrathecally produced anti-MBP (Warren, K. G. and Catz, I., Ann Neurol 209:20–25, 1986; and Catz, I. and Warren, K. G., Can J Neurol Sci 13:21–24, 1986). These antibodies are found predominantly in free (F) form during acute relapses and predominantly in bound (B) form when the disease is insidiously progressive (Warren, K. G. and Catz, I., Ann Neurol 209:20–25, 1986). During acute relapses, CSF anti-MBP titers correlated with disease activity (Warren, K. G. and Catz, I., Ann Neurol 21:183–187, 1987). Anti-MBP levels were also increased in patients with first attacks of optic neuritis and in most patients experiencing first attacks of MS (Warren, K. G., Catz, I., and Bauer, C., Ann Neurol 23:297–299, 1988; Warren, K. G. and Catz, I., J Neurol Sci 91:143–151, 1989).

Longitudinal kinetic studies of CSF anti-MBP levels in patients who enter the recovery phase subsequent to an acute relapse, demonstrated a gradual decline in F anti-MBP titers commensurate with a progressive rise in B fractions (Warren, K. G. and Catz, I., J Neurol Sci 91:143–151, 1989; Warren, K. G. and Catz, I., J Neurol Sci 88:185–194, 1988). In the remission phase, CSF anti-MBP may become undetectable suggesting an anti-MBP neutralization associated with inactive phases of MS (Warren, K. G. and Catz, I., J Neurol Sci 88:185–194, 1988). In contrast, chronic-progressive MS characterized by persistence of increased anti-MBP over long periods of time was associated with inhibition of anti-MBP neutralization (Warren, K. G. and Catz, I., J Neurol Sci 88:185–194, 1988). Recently a myelin basic protein antibody cascade, identified in the IgG fraction purified from CSF of MS patients, contained anti-MBP, antibodies which neutralize anti-MBP and antibodies which inhibit anti-MBP neutralization (Warren, K. G. and Catz, I., J Neurol Sci 96:19–27, 1990).

Our previous research has demonstrated from the B-cell autoimmune point of view that there are at least two distinct forms of MS with the majority of patients having auto antibodies to myelin basic protein (anti-MBP) and a lesser number having antibodies to proteolipid protein (anti-PLP) (Warren, K. G. et al., Ann. Neurol. 35, 280–289, 1994). In anti-MBP associated MS, acute relapses are associated with elevated Free (F)/Bound (B) anti-MBP ratios whereas the chronic progressive phase is characterized by lower F/B anti-MBP ratios, and patients in remission less frequently have mildly elevated anti-MBP titers (Warren, K. G. and Catz, I., J. Neurol. Sci. 88, 185–194, 1989).

It has been demonstrated that some of the proliferating T-cells in MS patients are directed towards MBP (Allegretta et al., Science, 247, 718–721, 1990) and that human T-cells can recognize multiple epitopes on the molecule (Richert et al., J. Neuroimmun 23, 55–66, 1989). MBP also appears to be capable of activating some T-cells without the involvement of antigen presenting cells (Altman et al., Eur. J. Immun. 17, 1635–1640, 1987). It is likely that small peptides of MBP may be recognized by T-cells without the requirement for intracellular processing, simply by their ability to bind class II major histocompatibility antigens on the surface of presenting cells.

Since experimental allergic encephalomyelitis (EAE), an accepted animal model of MS, can be induced by inoculating susceptible rodents with either MBP or PLP in conjunction with Freund's complete adjuvant, the process of MS demyelination may have an autoimmune mechanism (Fritz, R. B. et al., J. Immunol. 130, 1024–1026, 1983; Trotter, J. L. et al., J. Neurol. Sci. 79, 173–188, 1987). From B-cell autoantibody point of view, the MBP epitope targeted by the disease process has been localized proximal to the tri-Prolil sequence (residues—99—100—101—) to an area between residues 80 and 100 (Warren, K. G. et al., Ann. Neurol. 35, 280–289, 1994). This B-cell epitope overlaps the immunodominant epitope for T cells reactive to MBP, which are found in MS brain lesions (Oksenberg, J. R. et al., Nature, 362, 68–70, 1993).

Previous studies have shown that anti-MBP is neutralized by MBP. However, previous attempts to treat MS by intramuscular or subcutaneous administration of heterologous MBP have not been successful (Campbell, B., Vogel, R. J., Fisher, E. and Lorenz, R., Arch Neurol 29:10–15, 1973; Gonsette, R. E., Delmotte, P. and Demonty, L., J Neurol 216:27–31, 1977; and Romine, J. S. and Salk, J., In: Hallpike, J. F., Adams, C. W. M. and Tourtelotte, W. W., eds. Multiple sclerosis. Baltimore, Williams & Wilkins, 1982:621–630). The problem with using native MBP is two-fold. The protein is prepared from human brain samples and accordingly there is a potential danger that latent neuroviruses may be present in the sample. Secondly, although MBP is not normally an immunogen, it is possible that when administered to individuals with an altered immune system, MBP could act as an antigen and cause the production of antibodies against MBP.

Accordingly, the present invention determines whether anti-MBP purified from CSF of MS patients with acute relapses could be neutralized by selected peptides of human MBP (h-MBP). For this purpose, synthetic peptides covering the entire length of h-MBP were used to determine the possible epitope range on h-MBP which neutralizes anti-MBP obtained from these patients. Therefore selected peptides, which demonstrate neutralization of anti-MBP, can be used to treat MS more effectively than the full length MBP. These peptides are non-naturally occurring and as such no potential threat of neuroviruses would exist. Additionally, due to their small size, these peptides could not act as an immunogen. Therefore, the use of selected peptides as a treatment for MS, would overcome the problems identified with using the native protein.

Further the peptides of the present invention were investigated to determine their effectiveness in binding or modulating the production of MS anti-MBP in vivo.

SUMMARY OF INVENTION

According to the present invention there is provided, peptides which are substantially homologous in sequence to a part of the amino acid sequence of a human myelin basic protein. These peptides are capable of neutralizing or modulating the production of anti-MBP.

According to the present invention the peptides are of the formula:

$$R_1\text{-Val-His-Phe-Phe-Lys-Asn-Ile-}R_2$$

and salts thereof, wherein Val-His-Phe-Phe-Lys-Asn-Ile- is amino acid residues 87–93 of SEQ ID NO:1, and wherein $R_1$ and $R_2$ are independently selected from the group consisting of hydrogen, hydroxy, the residue of an amino acid and the residue of a polypeptide; provided that $R_1$ and $R_2$ are not both hydrogen or hydroxyl at the same time. The peptide can contain substitutions, deletions or additions thereof, provided that the peptide maintains its function of neutralizing or modulating the production of anti-MBP.

Examples of said peptides are selected from:
MBP75–95 (amino acid residues 75–95 of SEQ ID NO:1)
Lys Ser His Gly Arg Thr Gln Asp Glu Asn Pro Val Val His Phe Phe Lys Asn Ile Val Thr
MBP64–78 (amino acid residues 64–78 of SEQ ID NO:1)
Ala Arg Thr Ala His Tyr Gly Ser Leu Pro Gln Lys Ser His Gly
MBP61–75 (amino acid residues 61–75 of SEQ ID NO:1)
His His Pro Ala Arg Thr Ala His Tyr Gly Ser Leu Pro Gln Lys
MBP69–83 (amino acid residues 69–83 of SEQ ID NO:1)
Tyr Gly Ser Leu Pro Gln Lys Ser His Gly Arg Thr Gln Asp Glu
MBP80–97 (amino acid residues 80–97 of SEQ ID NO:1)
Thr Gln Asp Glu Asn Pro Val Val His Phe Phe Lys Asn Ile Val Thr Pro Arg
MBP91–106 (amino acid residues 91–106 of SEQ ID NO:1)
Lys Asn Ile Val Thr Pro Arg Thr Pro Pro Pro Ser Gln Gly Lys Gly
MBP84–93 (amino acid residues 84–93 of SEQ ID NO:1)
Asn-Pro-Val-Val-His-Phe-Phe-Lys-Asn-Ile
MBP85–94 (amino acid residues 85–94 of SEQ ID NO:1)
Pro-Val-Val-His-Phe-Phe-Lys-Asn-Ile-Val
MBP86–95 (amino acid residues 86–95 of SEQ ID NO:1)
Val-Val-His-Phe-Phe-Lys-Asn-Ile-Val-Thr
MBP87–96 (amino acid residues 87–96 of SEQ ID NO:1)
Val-His-Phe-Phe-Lys-Asn-Ile-Val-Thr-Pro Further according to the present invention there is provided pharmaceutical compositions, which comprises as an active ingredient a peptide as described above, either alone or in combination, in admixture with a pharmaceutical acceptable carrier.

Further according to the present invention, there is provided a method of treating multiple sclerosis comprising administering an effective amount of a peptide as, described above, either alone or in combination to effectively neutralize or modulate the production of anti-human myelin basic protein.

open circles: Bound (B) anti-MBP determined after acid hydrolysis of CSF immune complexes.
closed circles: Free (F) anti-MBP FIG. 5 - Control patients: CSF anti-MBP levels in 2 "time controls" (1F56, FIG. 5A and 3M66, FIG. 5B) and 2 "time-saline controls" (4M45, FIG. 5C and 5M59, FIG. 5D). In all four patients F and B anti-MBP remained constantly elevated at baseline level when CSF was sampled every 30 minutes for the first two hours as well as 24 hours later. Symbols as in FIG. 4.

FIG. 6 - Interpatient peptide studies: CSF anti-MBP levels in a group of four patients (10F38, FIG. 6A; 13F43, FIG. 6C; 5M59, FIG. 6D; and 3M66, FIG. 6G) who received increasing amounts (1, 2.5, 5 and 10 mg respectively) of a non-binding, control synthetic peptide MBP35–58 and a paired group of four other MS patients (6F53, FIG. 6B; 8M41, FIG. 6D; 4M45, FIG. 6F; and 1F56, FIG. 6H) who received increasing amounts (1, 2.5, 5 and 10 mg respectively) of the anti-MBP binding synthetic peptide MBP75–95. CSF F anti-MBP was bound in a dose-dependent fashion by peptide MBP75–95 and it did not react with peptide MBP35–58. Bound anti-MBP remained virtually unaffected.

FIG. 7 - Intrapatient peptide studies: when MS patients were either "time controls" (1F56, FIG. 7C and 3M66, FIG. 7D) or "time-saline controls" (5M59, FIG. 7A and 4M45, FIG. 7B), or when they received the non-binding, control peptide MBP35–58 (5M59 and 3M66) their F and B CSF anti-MBP levels remained unaffected. In contrast, when the same patients 4M45, 1F56 and 3M66 later received 5–10 mg of the anti-MBP binding peptide MBP75–95, their F anti-MBP became undetectable for periods up to 7 days and returned to baseline level between 10 and 21 days.

Figure 8:
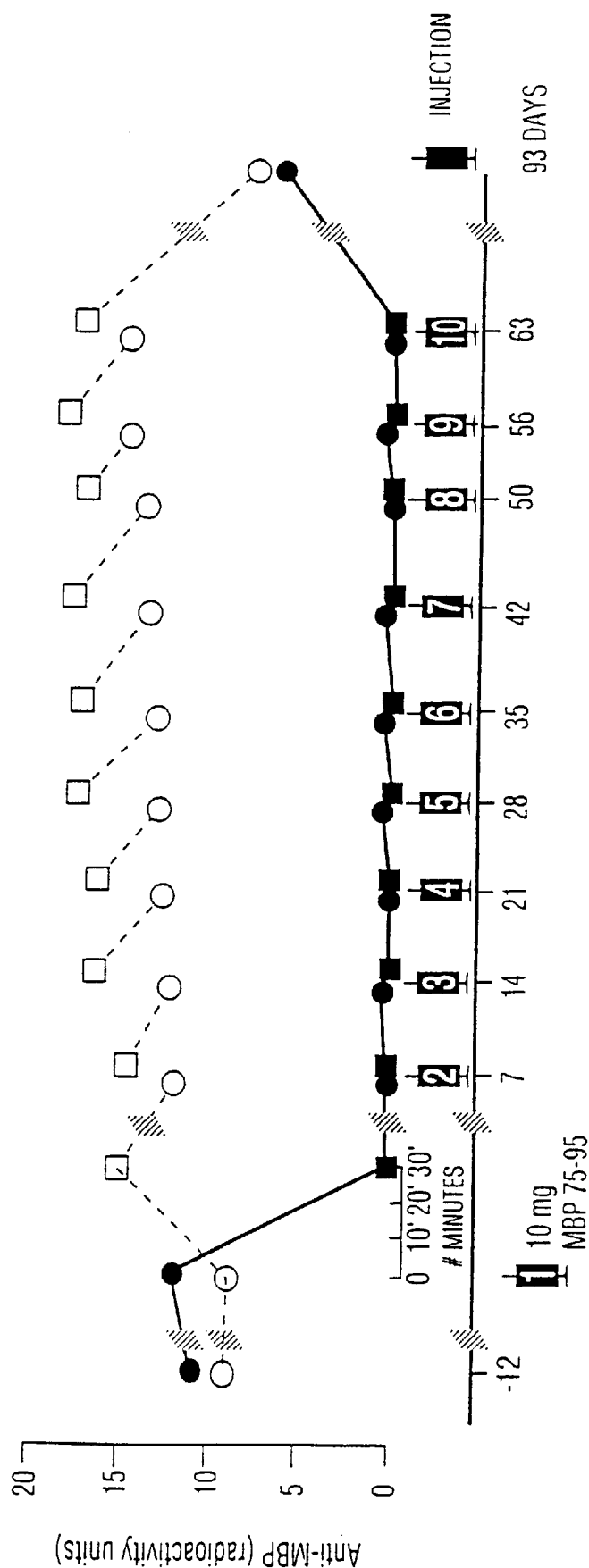

FIG. 8 - Repeated intrathecal synthetic peptide injections: a patient with chronic progressive MS received 10 weekly injections of 10 mg MBP75–95 inoculated directly into the CSF; F and B titers of anti-MBP were measured before (circles) and 30 minutes after (squares) each inoculation. F anti-MBP (closed circles and squares) was rendered undetectable for the 10 week period while B antibody remained essentially unchanged (open circles and squares).

Figure 9:
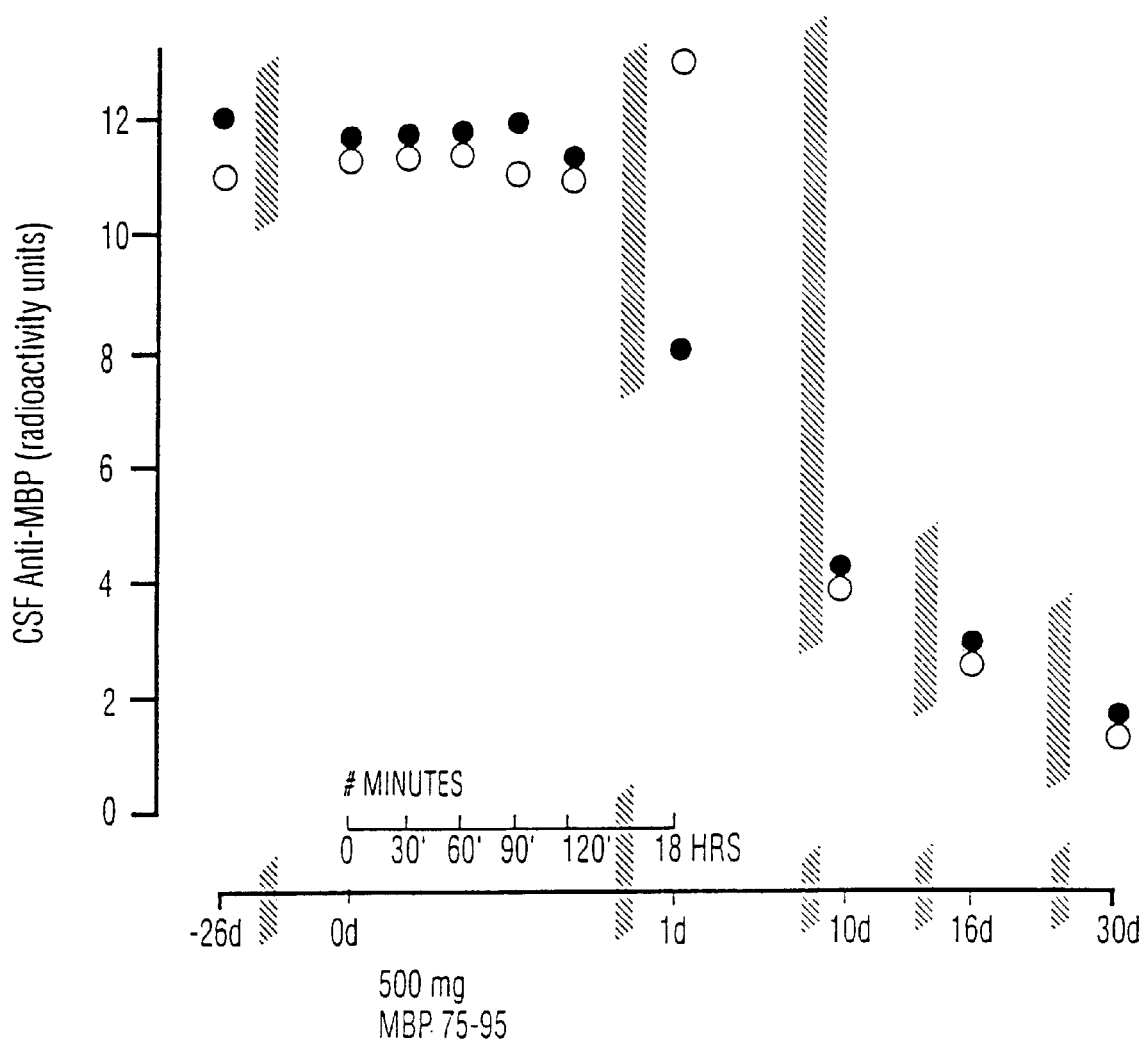

FIG. 9 - Intravenous synthetic peptide administration: CSF anti-MBP levels following a single intravenous injection of 500 mg MBP75–95; both F and B anti-MBP levels declined significantly when tested 10, 16 and 30 days after injection. Symbols as in FIG. 4.

Figure 10:
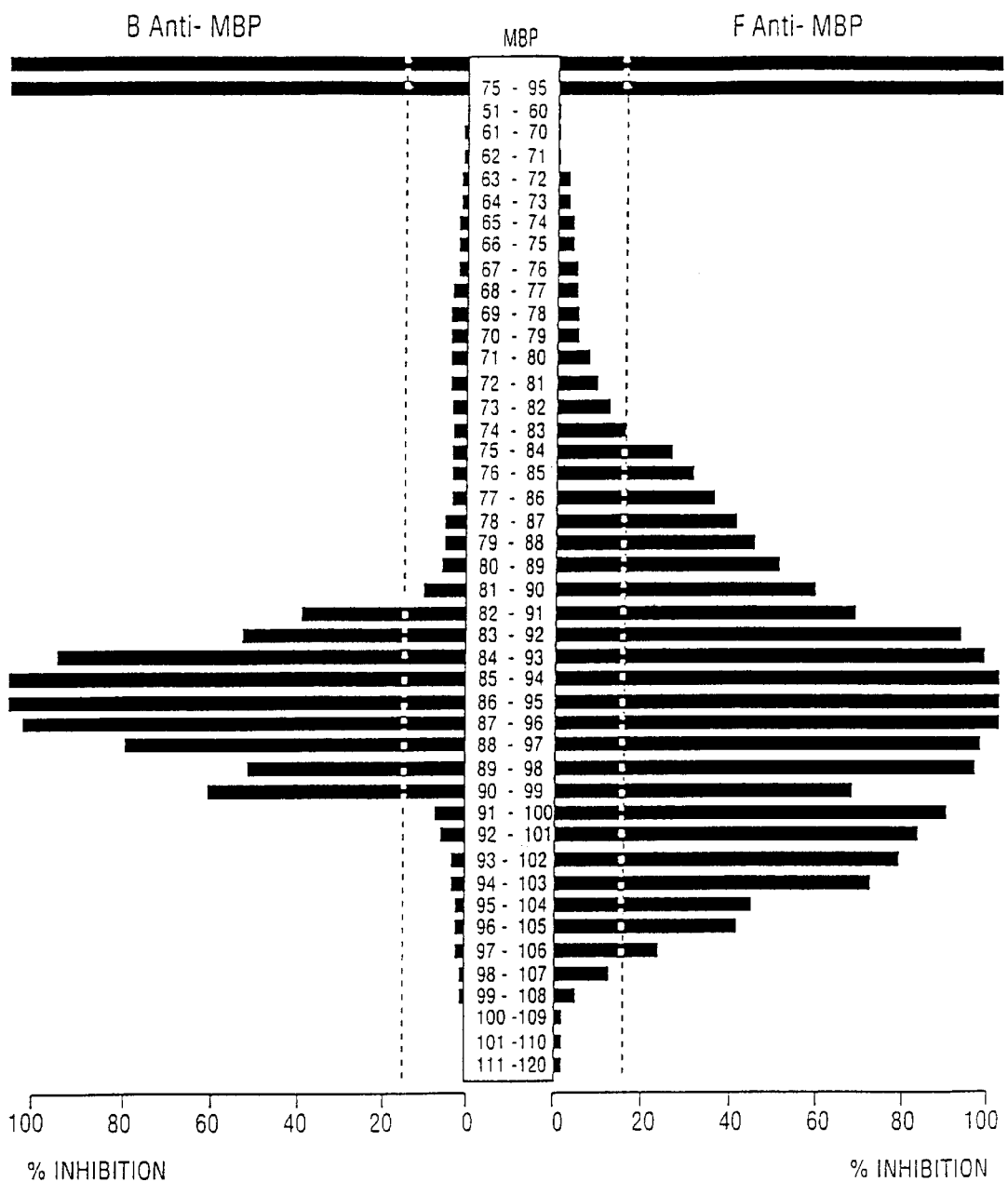

FIG. 10 - Further refinement of the MBP epitope for MS anti-MBP using a set of 41 decapeptides which covered the area between residues 61 and 110.

Legend:
bars represent percent inhibition=100−radioactivity units
MBP and peptide MBP75–95 were used as positive controls and produced complete (100%) inhibition of both F and B antibody
peptides MBP51–60 and MBP 111–120 were used as negative controls and produced insignificant inhibition (0–10%) of F and B anti-MBP
decapeptides MBP84–93, MBP85–94, MBP86–95 and MBP87–96 which produced maximum inhibition (90–100%) of both F and B antibody are highly associated with the MBP epitope
dotted line: 95% confidence limits of the inhibition assay

DETAILED DESCRIPTION OF THE INVENTION

The present invention is directed to selected peptides, which are substantially homologous in sequence to a part of the amino acid sequence of a human myelin basic protein. By 'substantially homologous' it is meant that some variation between the amino acid sequence of a human myelin basic protein and the peptides can exist provided that the peptides, with a variation in amino acid sequence, still function in their intended use, i.e. to neutralize or to modulate the production of antibodies to human myelin basic protein (anti-MBP). Given the teachings of the present invention, it would be readily apparent to persons skilled in the art to determine, empirically, what variation can be made to the sequence of the selected peptides without affecting the function of the peptides.

Based on the present invention, on the basis of the competitive inhibition assays using a series of 41 decapeptides, the MBP epitope for MS anti-MBP has been localized to an area between amino acid 82 and amino acid 98, greater than 40% inhibition of bound anti-MBP and greater than 60% inhibition of free anti-MBP. Based on the highest level of inhibition, the MBP epitope for MS anti-MBP is probably between amino acid 84 and amino acid 96.

The smallest common region of the effective decapeptides is from amino acid 87 to amino acid 93. Thus, according to the present invention, the peptides can be illustrated by the following formula:

$$R_1\text{-Val-His-Phe-Phe-Lys-Asn-Ile-}R_2$$

and salts thereof, wherein Val-His-Phe-Phe-Lys-Asn-Ile- is amino acid residues 87–93 of SEQ ID NO:1, and wherein $R_1$ and $R_2$ are independently selected from the group consisting of hydrogen, hydroxy, the residue of an amino acid and the residue of a polypeptide; provided that $R_1$ and $R_2$ are not both hydrogen or hydroxyl at the same time.

The 7 amino acids spanning amino acid position 87 to 93 would probably not be large enough to effectively bind anti-MBP. Thus, $R_1$ and $R_2$ cannot both be hydrogen or both be hydroxy at the same time.

When $R_1$ or $R_2$ is an amino acid, the amino acid can be selected from naturally occurring amino acids. $R_1$ or $R_2$ are not restricted to the amino acids occurring upstream or downstream of Val87 and Ile93 in the human myelin basic protein, as shown in SEQID NO: 1. Various modification, including substitutions, additions or deletions in the upstream and downstream sequences of $R_1$ and $R_2$ can be used. In addition, modification, including substitutions, additions or deletions can be made to the sequence -Val-His-Phe-Phe-Lys-Asn-Ile (amino acid residues 87–93 of SEQ ID NO:1), provided that the peptides so produced still function in their intended use; i.e., to neutralize or modulate the production of antibodies to myelin basic protein.

The term "residue of polypeptide" or "polypeptide residue" is meant to include di, tri, and higher polypeptides including proteins or fragments thereof. As above, when $R_1$ or $R_2$ is a polypeptide residue, $R_1$ or $R_2$ are not limited to the peptides occurring upstream or downstream of Val87 and Ile93, in the human myelin basic protein. Any polypeptide residue can be used.

$R_1$ and/or $R_2$ could be a repeat of the sequence—Val-His-Phe-Phe-Lys-Asn-Ile, or modifications thereof, including substitutions, additions or deletions. Thus, the peptide could contain multiple copies of the anti-MBP binding site (epitope).

The compounds of the present invention can be prepared according to conventional and well-known methods of synthesizing polypeptides. Also included within the scope of the term 'peptide' are peptides produced from controlled hydrolysis of the naturally occurring myelin basic proteins to produce the selected peptides of the present invention. Also included within the scope of the term 'peptide' are peptides produced by recombinant DNA technology. Knowing the sequence of the selected peptides, as disclosed in the present invention, it is within the scope of the present invention to determine an appropriate DNA sequence, which will code for the selected amino acid sequence. The appropriate DNA sequence can be produced by conventional and well-known methods of synthesizing DNA sequences. The DNA sequences so produced can then be cloned into appropriate cloning vehicles and used to transform an appropriate host cell to produce the recombinant peptide. All of the methodology referred to above is conventional and well-known to persons skill in the art.

The peptides, of the present invention, are substantially homologous in sequence to a part of the amino acid sequence of a human myelin basic protein. By 'a part of the amino acid sequence' it is meant that the sequence can be of any length provided that the amino acid sequence is long enough to function to neutralize or modulate the production of anti-human myelin basic protein or anti-MBP but not of a length which would result in the prior art problems when the peptides are used for in vivo treatment of Multiple Sclerosis. According to the present invention the peptides can be at least 10 amino acids in length. In one example of the present invention the peptides can be from about 10 amino acid residues to about 25 amino acid residues. If the peptides of the present invention are used as part of a fusion protein, the overall size of the peptide can be much larger.

According to one embodiment of the present invention it has been determined that selected peptides substantially corresponding to the amino acid sequence of the h-MBP are effective in neutralizing or modulating the production of anti-MBP. These peptides correspond to the amino acid sequence of the h-MBP from about amino acid residue 61 to about amino acid residue 106. In one example these peptides correspond to the amino acid sequence of the h-MBP from about amino acid residue 75 to about amino acid residue 106, when the peptides are used for the neutralization of free anti-MBP. In a further example, these peptides correspond to the amino acid sequence of the h-MBP from about amino acid residue 82 to about amino acid residue 99, when the peptides are used for the neutralization or modulation of the production of bound anti-MBP. Therefore the peptides are selected from 10 amino acid residues to 25 amino acid residues taken from a continuous amino acid sequence within the sequence shown below (amino acid residues 61–106 of SEQ ID NO:1), provided that said sequence can neutralize or modulate the production of the anti-myelin basic protein.

of hydrogen, hydroxy, the residue of an amino acid and the residue of a polypeptide; provided that $R_1$ and $R_2$ are not both hydrogen or hydroxyl at the same time. The peptide can contain substitutions, deletions or additions thereof, provided that the peptide maintains its function of neutralizing or modulating the production of anti-MBP.

Examples of peptides are selected from:

MBP84–93 (amino acid residues 84–93 of SEQ ID NO:1) Asn-Pro-Val-Val-His-Phe-Phe-Lys-Asn-Ile MBP85–94 (amino acid residues 85–94 of SEQ ID NO:1) Pro-Val-Val-His-Phe-Phe-Lys-Asn-Ile-Val MBP85–94 (amino acid residues 85–94 of SEQ ID NO:1) Val-Val-His-Phe-Phe-Lys-Asn-Ile-Val-Thr MBP87–96 (amino acid residues 87–96 of SEQ ID NO:1) Val-His-Phe-Phe-Lys-Asn-Ile-Val-Thr-Pro The potential role of anti-MBP in the pathogenesis of MS continues to be explored. Increased anti-MBP titers in patients with active MS were initially reported by Panitch et al (Panitch, H. S., Hooper, C. S., and Johnson, K. P., Arch Neurol 37:206–209, 1980) who used a solid phase radioimmunoassay with guinea-pig MBP. Patients with acute MS relapses have usually increased anti-MBP predominantly in free form, while some patients in clinical remission may have undetectable anti-MBP levels. During the transition phase from an acute relapse to remission, titers of free anti-MBP progressively decrease over weeks or months, while bound fractions of the antibody rise as compared to their initial value. In other patients in remission, it is possible to observe low titers of free and bound anti-MBP, usually

```
Amino Acid residues 61–106 of SEQ ID NO:1
61
His His Pro Ala Arg Thr Ala His Tyr Gly Ser Leu Pro Gln Lys Ser His Gly Arg Thr Gln Asp Glu Asn Pro Val Val His Phe Phe Lys Asn Ile Val Thr Pro Arg Thr Pro Pro Pro Ser Gln Gly Lys Gly
                                    106
```

Examples of peptides are selected from the group consisting of:

MBP61–75 (amino acid residues 61–75 of SEQ ID NO:1) His His Pro Ala Arg Thr Ala His Tyr Gly Ser Leu Pro Gln Lys MBP64–78 (amino acid residues 64–78 of SEQ ID NO:1) Ala Arg Thr Ala His Tyr Gly Ser Leu Pro Gln Lys Ser His Gly MBP69–83 (amino acid residues 69–83 of SEQ ID NO:1) Tyr Gly Ser Leu Pro Gln Lys Ser His Gly Arg Thr Gln Asp Glu MBP75–95 (amino acid residues 75–95 of SEQ ID NO:1) Lys Ser His Gly Arg Thr Gln Asp Glu Asn Pro Val Val His Phe Phe Lys Asn Ile Val Thr MBP80–97 (amino acid residues 80–97 of SEQ ID NO:1) Thr Gln Asp Glu Asn Pro Val Val His Phe Phe Lys Asn Ile Val Thr Pro Arg MBP91–106 (amino acid residues 91–106 of SEQ ID NO:1) Lys Asn Ile Val Thr Pro Arg Thr Pro Pro Pro Ser Gln Gly Lys Gly In one embodiment of the present invention, the peptides are represented by the formula:

$R_1$-Val-His-Phe-Phe-Lys-Asn-Ile-$R_2$ and salts thereof, wherein Val-His-Phe-Phe-Lys-Asn-Ile is amino acid residues 87–93 of SEQ ID NO:1, and wherein $R_1$ and $R_2$ are independently selected from the group consisting with a F/B ratio below unity, suggesting that anti-MBP neutralizing antibody(ies) are bound to anti-MBP. Occasionally, patients who fit the criteria of clinically definite MS or patients who had neuropathologically confirmed MS had undetectable anti-MBP during active phases of their disease. It is possible that such patients have antibodies to other myelin proteins. The absence of a specific antibody scenario does not negate the potential importance of anti-MBP in the mechanism of demyelination in the majority of MS patients.

Recently, an MBP antibody cascade was observed in the IgG fraction purified from MS CSF (Warren, K. G. and Catz, I., J Neurol Sci 96:19–27, 1990). Primary antibodies to MBP in both free and bound forms occur in association with active disease: F/B ratios are above unity in patients with acute relapses, and below unity in patients with chronic progressive disease (Warren, K. G. and Catz, I., Ann Neurol 209:20–25, 1986; Catz, I. and Warren, K. G., Can J Neurol Sci 13:21–24, 1986; and Warren, K. G. and Catz, I., Ann Neurol 21:183–187, 1987). Secondary antibodies which neutralize anti-MBP appear when the disease becomes inactive. Tertiary antibodies which inhibit anti-MBP neutralization are present when the disease is chronically progressive and fails to become inactive. The fact that an MBP antibody cascade is associated with distinct phases of MS suggests its possible importance vis-a-vie the natural history of this illness.

Although anti-MBP can be detected in CSF of patients with active MS, their direct role in the pathogenesis of demyelination remains to be confirmed. The involvement of anti-MBP in the mechanism of MS could best be determined by their neutralization, in vivo, perhaps by administration of selected peptides and monitoring the clinical course of the disease. If anti-MBP is (are) the only primary antibody(ies) associated with demyelination in MS, it may be possible to block this process by intrathecal, and/or intravenous, and/or oral administration of selected MBP peptides which would neutralize anti-MBP and would promote tolerance to MBP in situ. Other human myelin proteins may also be involved with the demyelination in MS and accordingly, it is within the scope of the present invention to use peptides substantially homologous in sequence to a part of the amino acid sequence of these other myelin proteins to neutralize the corresponding antibodies. Although previous attempts to treat MS by intramuscular or subcutaneous administration of heterologous MBP have not been entirely successful (Campbell, B., Vogel, R. J., Fisher, E. and Lorenz, R., Arch Neurol 29:10–15, 1973; Gonsette, R. E., Delmotte, P. and Demonty, L. J Neurol 216:27–31, 1977; and Romine, J. S. and Salk, J., In: Hallpike, J. F., Adams, C. W. M. and Tourtelotte, W. W., eds. Multiple sclerosis. Baltimore. Williams & Wilkins, 1982:621–630), intrathecal and/or intravenous administration of MBP peptides which neutralize or modulate the production of anti-MBP, according to the present invention, has demonstrated more beneficial results.

The animal model of MS, experimental allergic encephalomyelitis, is a T cell mediated demyelinating disease. EAE can be ameliorated by intraperitonial inoculation of affected mice with MBP synthetic peptides (Gaur, A. et al., Science 258, 1491–1494, 1992). Furthermore, administration of high doses MBP deleted autoreactive T cells and abrogated clinical and pathological signs of EAE in mice (Critchfield, J. M. et al., Science 263, 1139–1143, 1994). Even oral administration of MBP modulated EAE by inducing peripheral tolerance (Chen, W. et al., Science. 265, 1237–1240, 1194). In a recent double blind pilot trial it has been suggested that tolerization can be induced in MS patients by oral administration of myelin antigens (Weiner, H. L. et al., Science 259, 1321–1324, 1993). A combination of myelin antigens or synthetic peptides of these antigens administered by oral, and/or intravenous and/or intrathecal routes may be required to modulate the T cells, B cells and macrophages involved in the destruction of myelin in MS patients.

Accordingly, this invention also relates to pharmaceutical compositions containing as an active ingredient a peptide as described above, either alone or in combination, in admixture with a pharmaceutical acceptable carrier. Examples of pharmaceutical acceptable carriers are well known in the art, and include for example normal saline.

The peptides of the present invention can be administered to humans for the treatment or modulation of Multiple Sclerosis. The therapeutic dose, for intravenous and/or oral administration, for the treatment of MS may be from about 1.0 mg per kilogram of body weight to about 10.0 mg per kilogram of body weight. If the administration is intrathecal, the dose will be from about 1 to 10 mg. In one example of the present invention, the peptide is administered either intravenously or intrathecally, or in combination. The peptides can be administered as a single or sequential dose, as may be required.

While this invention is described in detail with particular reference to preferred embodiments thereof, the following examples, are offered to illustrate but not limit the invention.

EXAMPLE 1

In Vitro Neutralization of Anti-Human Myelin Basic Protein

Figure 1:
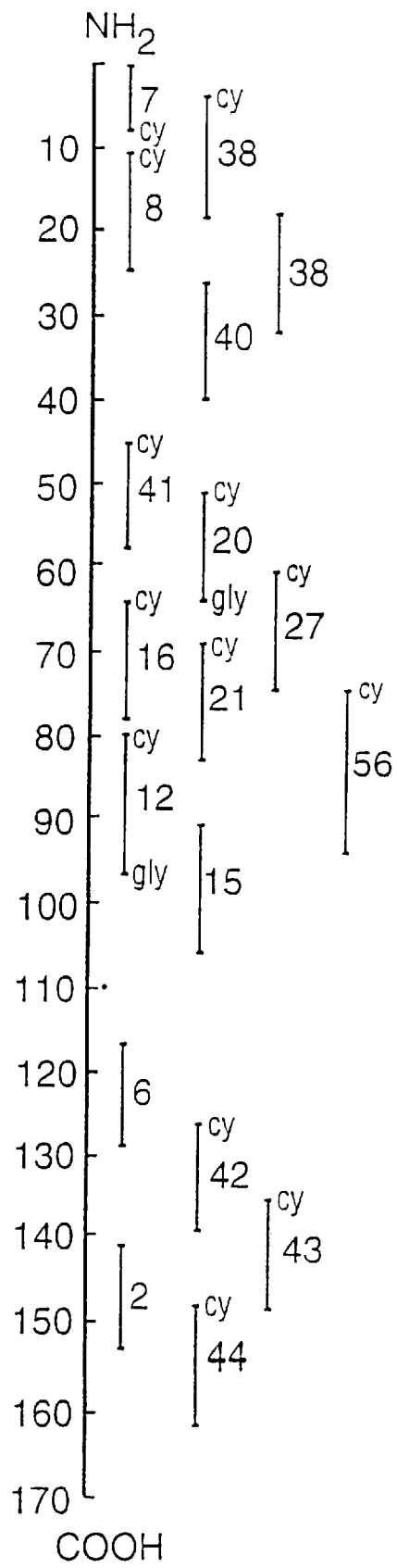
FIG. 1 shows the localization of eighteen synthetic peptides (small numbers) in relation to the intact human-MBP molecule. Peptides are represented by vertical bars placed next to their corresponding region on the MBP molecule. Large numbers represent amino acid residues on human MBP.

FIG. 1 shows the localization of 18 peptides of h-MBP used in this study in relation to the intact MBP molecule. Native MBP was isolated from non-MS brain tissue (Diebler, G. E., Martenson, R. E., Kies, M. W., Prep Biochem 2:139–165, 1972) and further purified by gel filtration. The final antigen preparations were checked for purity by SDS-polyacrylamide gel electrophoresis. Only preparations that migrated at the molecular weight of 18.5 KD were used in further studies. Purified MBP was used in antigen-specific affinity chromatography, in neutralization studies and in the solid phase anti-MBP radioimmunoassay.

Eighteen peptides covering the length of h-MBP and containing between 8 and 25 amino acid residues were synthesized by the Fmoc method as previously described (Groome, N. P., Dawkes, A, Barry, R. et al. J Neuroimmun 19:305–315, 1988). Peptide purity was checked by reverse-phase high pressure liquid chromatography with a C18 column and water/acetonitrile gradient (0.1% TFA). Amino acid analysis of peptides was also performed using standard analysis. Many of the peptides used in this study contained an unnatural cysteine residue as they were made to function as immunogens. This is unlikely to affect the present findings.

Cerebrospinal fluid (CSF) was obtained within a week from the onset of symptoms from 35 patients with acute MS relapses and IgG levels were determined by nephelometry. CSF samples used in this study were selected to have initially high absolute IgG levels ($\geq 0.80$ g/l) and increased titers of anti-MBP (F/B ratio>1.0). All MS patients had clinically definite disease.

IgG was purified from concentrated CSF of patients with acute MS by protein A-Sepharose (Pharmacia™) affinity chromatography as previously described (Warren, K. G. and Catz, I., J Neurol Sci 96:19–27, 1990). The purity of each IgG preparation was checked by polyacrylamide gel electrophoresis and isoelectric focusing. When elevated anti-MBP levels from purified IgG were absorbed to zero with MBP, the post-absorption supernatants contained residual IgG.

Purified MBP was coupled to CNBr-activated Sepharose 4B (Pharmacia™) according to the manufacturer's instructions. Purified CSF IgG containing increased anti-MBP levels from 35 patients with acute MS relapses was used as starting samples to isolate unbound anti-MBP by MBP-Sepharose affinity chromatography (Warren, K. G. and Catz, I., J Neurol Sci 103:90–96, 1991). Purified anti-MBP samples were compared with the initial IgG source by poly-acrylamide gel electrophoresis. When purified anti-MBP was absorbed to zero with MBP, the post-absorption supernatants contained no residual IgG.

Constant amounts of anti-MBP (15 radioactivity binding units corresponding to 100 for scale expansion purposes =%O) were incubated with increasing amounts of h-MBP (0–1000 ng) or individual peptides of MBP (0–10,000 ng) in a liquid phase assay and after 1.5 hours incubation, free anti-MBP levels were determined in all mixtures. Anti-MBP isolated from 7 individual MS patients or pooled anti-MBP from 10 different MS patients were used in neutralization experiments. Calf thymus histone and human serum albumin were used as negative antigen controls (range: 10–1000 ng). One monoclonal antibody to peptide MBP64–78 (clone 26) and a polyclonal rabbit antiserum to peptide MBP1–8 (R155) were used as positive antibody controls (Groome, N., Harland, J., and Dawkes, A., Neurochem Int 7:309–317, 1985; Barry, R., Payton, M., and Groome, N., Neurochem Int 2:291–300, 1991). Another mouse monoclonal antibody to epitope 45–50 (clone 16) was used as negative antibody control.

Anti-MBP levels were determined by a solid phase radio-immunoassay with human MBP (Warren, K. G. and Catz, I., Ann Neurol 209:20–25, 1986; Warren, K. G. and Catz, I., Ann Neurol 21:183–187, 1987; and Warren, K. G. and Catz, I., J Neurol Sci 91:143–151, 1989). Free anti-MBP levels were measured in all fractions from affinity chromatographies and in all neutralization mixtures. All individual samples were run in quadruplicate using the same iodinated material in order to minimize between-assay variability.

Figure 2:
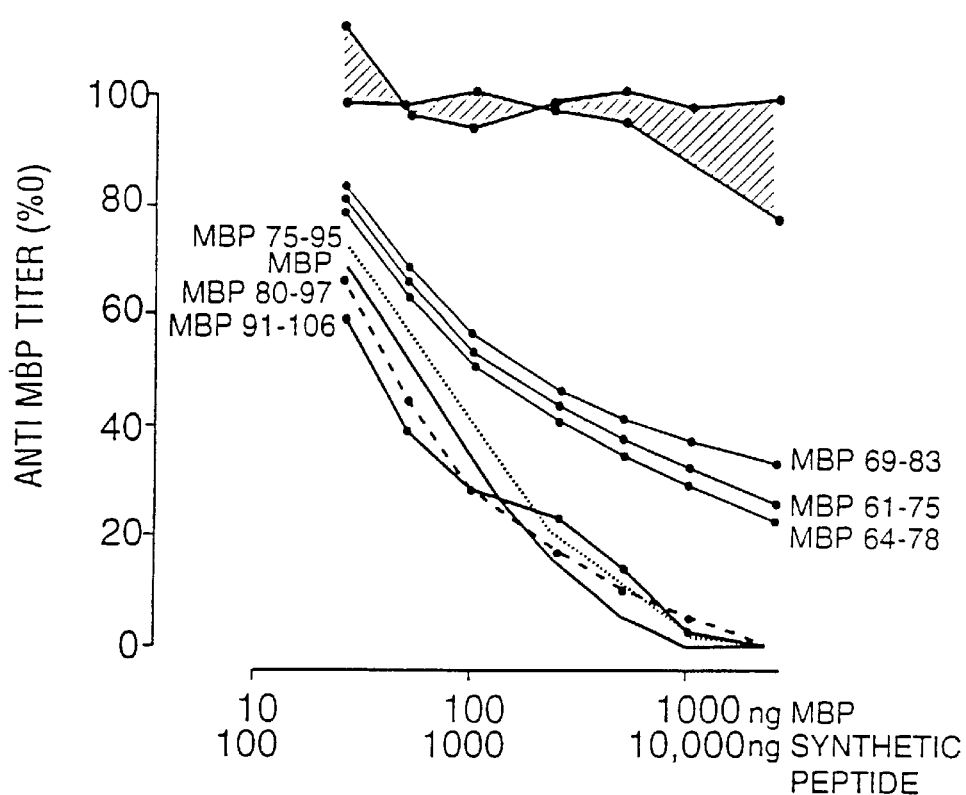
FIG. 2 shows inhibition curves of anti-MBP, purified and pooled from 10 different multiple sclerosis patients, by human MBP and MBP-peptides.

Purified anti-MBP was completely neutralized by MBP and by peptides MBP80–97, MBP91–106 and MBP75–95, and was partially neutralized by peptides MBP64–78, MBP69–83 and MBP61–75 (Table 1 and FIG. 2). The remaining twelve peptides did not neutralize purified anti-MBP and their kinetic curves fell within the striped area shown in FIG. 2. Calf thymus histone and human serum albumin did not react with purified anti-MBP even at concentrations as high as 1000 ng. Clone 26 was only inhibited by peptide MBP64–78. R155 was only inhibited by peptide MBP1–8. Clone 16 did not react with MBP or any of the peptides (for clarity of the figure, control data are not illustrated). The control samples demonstrate the validity of the neutralization approach as each control antibody was neutralized completely by the expected peptide and by none of the other peptides. This shows that even the high peptide concentrations (10,000 ng) specificity of recognition was observed.

TABLE 1

| PEPTIDE NUMBER | HUMAN MBP SEQUENCE | REACTIVITY WITH ANTI-MBP |
| --- | --- | --- |
| 7 | 1–8 Cy | − |
| 38 | Cy 4–18 | − |
| 8 | Cy 11–24 | − |
| 39 | 18–32 | − |
| 40 | 26–40 | − |
| 41 | Cy 35–58 | − |
| 20 | Cy 51–64 Gly | − |
| 16 | Cy 64–78 | + |
| 27 | Cy 61–75 | + |
| 21 | Cy 69–83 | + |
| 56 | Cy 75–95 | ++ |
| 12 | Cy 80–97 Gly | ++ |
| 15 | Cy 91–106 | ++ |
| 6 | 117–129 | − |
| 42 | Cy 127–140 | − |
| 43 | Cy 136–149 | − |
| 2 | 141–155 | − |
| 44 | Cy 149–162 | − |

++ complete neutralization
+ partial neutralization
− insignificant reactivity

Figure 3:
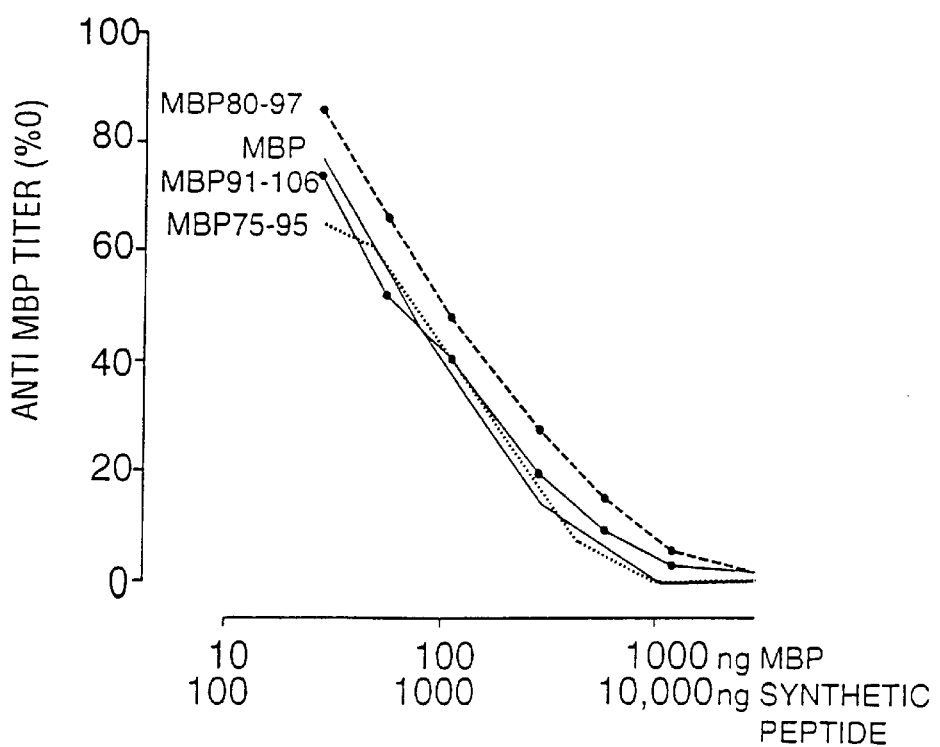
FIG. 3 shows the neutralization of anti-MBP isolated from an individual multiple sclerosis patient by human MBP and peptides MBP80–97; MBP91–106 and MBP75–95.

Anti-MBP purified from 7 individual MS patients was completely neutralized by h-MBP and peptides MBP80–97, MBP91–106 and MBP75–95 (see FIG. 3 as an illustrative example). Due to the limited amount of antibody obtained from individual MS patients, anti-MBP was not reacted with the remaining 15 peptides.

As noted previously, anti-MBP was neutralized with peptides spanning from about amino acid residue 61 to about amino acid residue 106. The peptides which did not neutralize anti-MBP cover both the amino (about residues 1 to 63) and the carboxyl (about residues 117 to 162) terminals of h-MBP. It appears that peptides from different non-overlapping regions of MBP neutralize the same antibody(ies). This might be explained if the antibodies recognize a discontinuous (assembled) epitope containing amino acids from different regions. A similar phenomenon has been previously observed by Hruby et al (Hruby, S., Alvord, E. C., Groome, N. P. et al, Molec Immun 24: 1359–1364, 1987) who showed that a rat monoclonal antibody had a major epitope in MBP sequence 112–121 but a strong cross-reaction with another epitope in peptide 39–91. This is more likely than the possibility that the antibody is cross-reactive with two completely different sequences which did not form a discontinuous epitope (Hruby, S., Alvord, E. C., Martenson, R. E., et al. J Neurochem 44:637–650, 1985). The neutralization data could be explained by the ability of peptides from different sections of MBP to each partially occupy the antibody binding pocket by interacting with different antibody amino acid side chains. This explanation fits the observation that the peptides giving complete inhibition (MBP80–97, MBP91–106 and MBP75–95) are approximately 100 times less effective on a molar basis than intact MBP at causing inhibition. By the hypothesis advanced above, this could be due to each peptide clone being unable to achieve the binding energy of the original MBP epitope.

EXAMPLE 2

Figure 4:
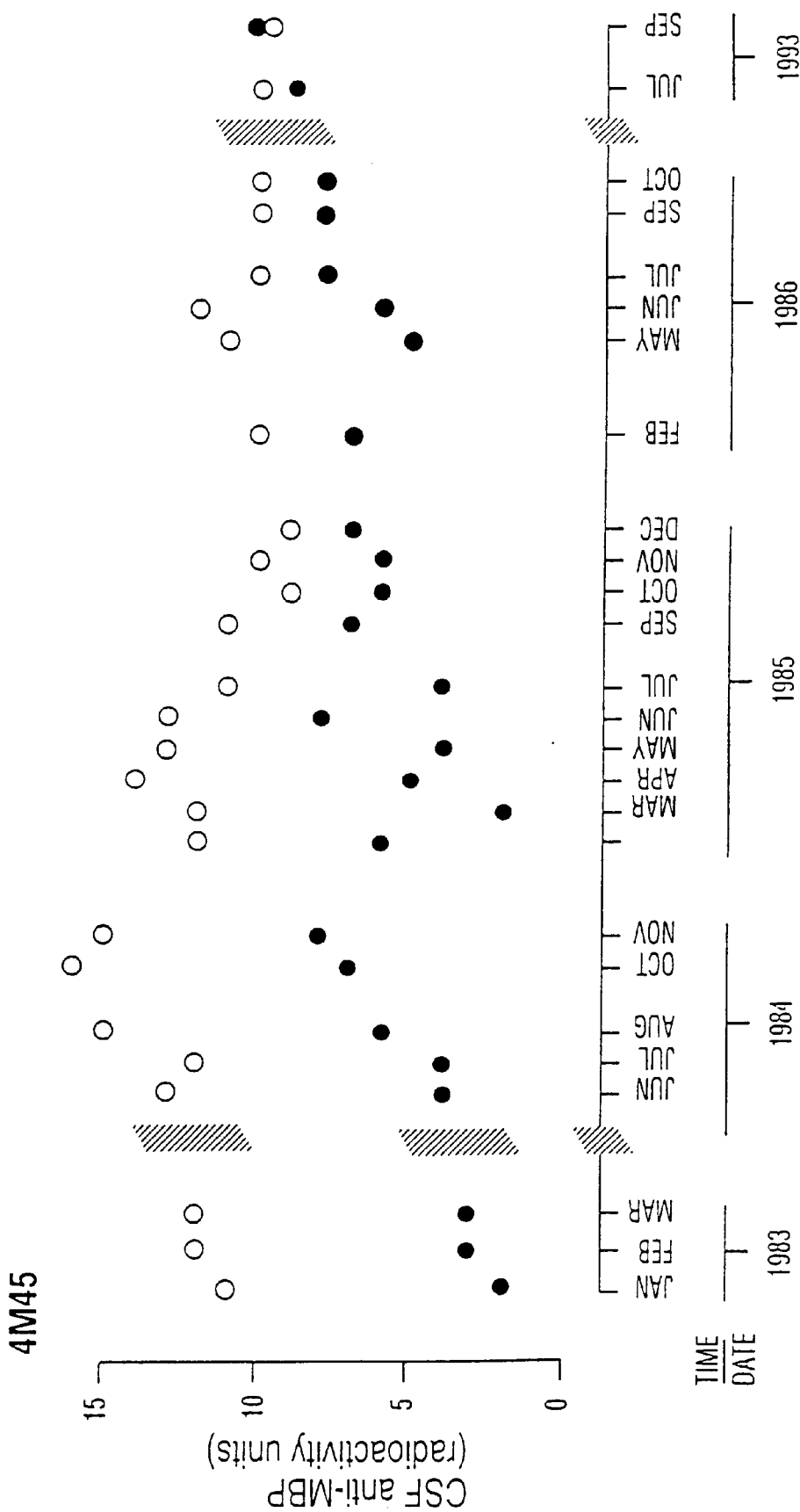
FIG. 4 - Longitudinal monitoring of CSF anti-MBP titers in a patient with chronic progressive MS:
F (Free) and B (Bound) levels of anti-MBP were persistently elevated when sampled 26 times over a period of 11 years from 1983 to 1993.
cpm: counts per minute $$\text{radioactivity units} = \frac{\text{cpm sample} - \text{cpm blank}}{\text{cpm total} - \text{cpm blank}}$$

In Vivo Neutralization or Modulation of Production of Anti-Human Myelin Basic Protein Patient Selection and Control Studies Patients who participated in this research project were seen in the Multiple Sclerosis Patient Care and Research Clinic of the University of Alberta, Edmonton, Canada. The patients have been diagnosed as having multiple sclerosis by Schumacher criteria (1965) and confirmed by magnetic resonance imaging of the brain and/or CSF immunochemistry profiles. In order to illustrate that in chronic progressive MS anti-MBP was persistently elevated over long periods of time, months to years, patients had repeated lumbar punctures with monitoring of F and B anti-MBP. In such a patient with chronic progressive MS, it was observed that the autoantibody remained persistently elevated for periods as long as 11 years and that spontaneous decline of anti-MBP levels does not occur (FIG. 4 is an illustrative example).

Figure 5A:
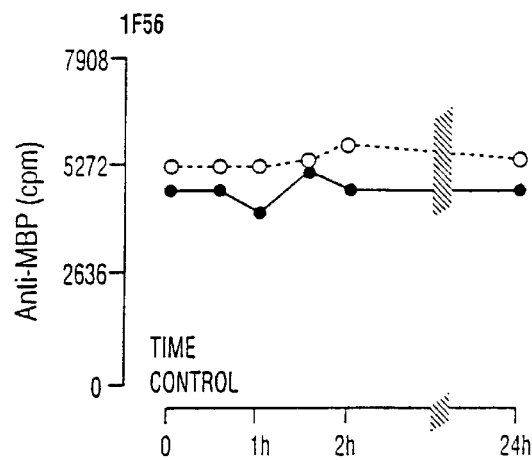
Figure 5B:
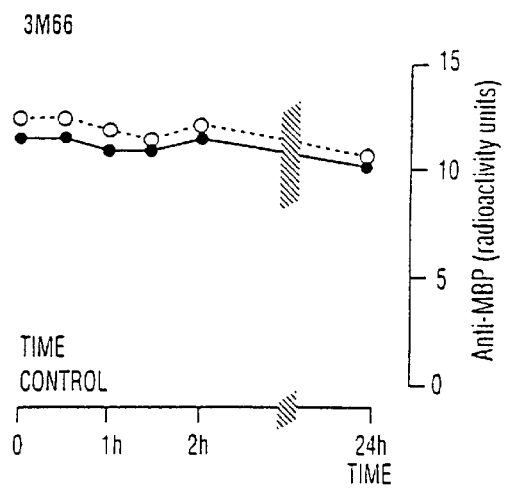

In order to determine that initially elevated CSF anti-MBP levels remained relatively constant over 24 hours, 2 patients (1 F56 and 3M66) had repeated CSF sampling every 30 minutes for 2 hours as well as 24 hours later with F and B anti-MBP monitoring (FIGS. 5A and 5B, respectively). Patients 1F56 and 3M66 served as "time controls". F and B anti-MBP levels remained constantly elevated when CSF was sampled every 30 minutes for 2 hours as well as 24 hours later.

Figure 5C:
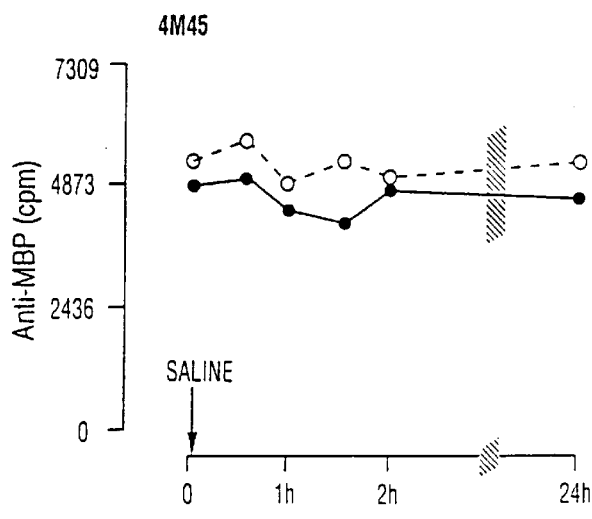
Figure 5D:
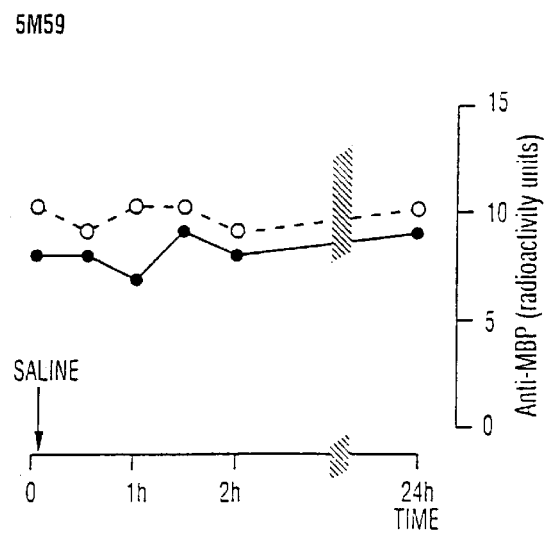
Figures 6A, 6B:
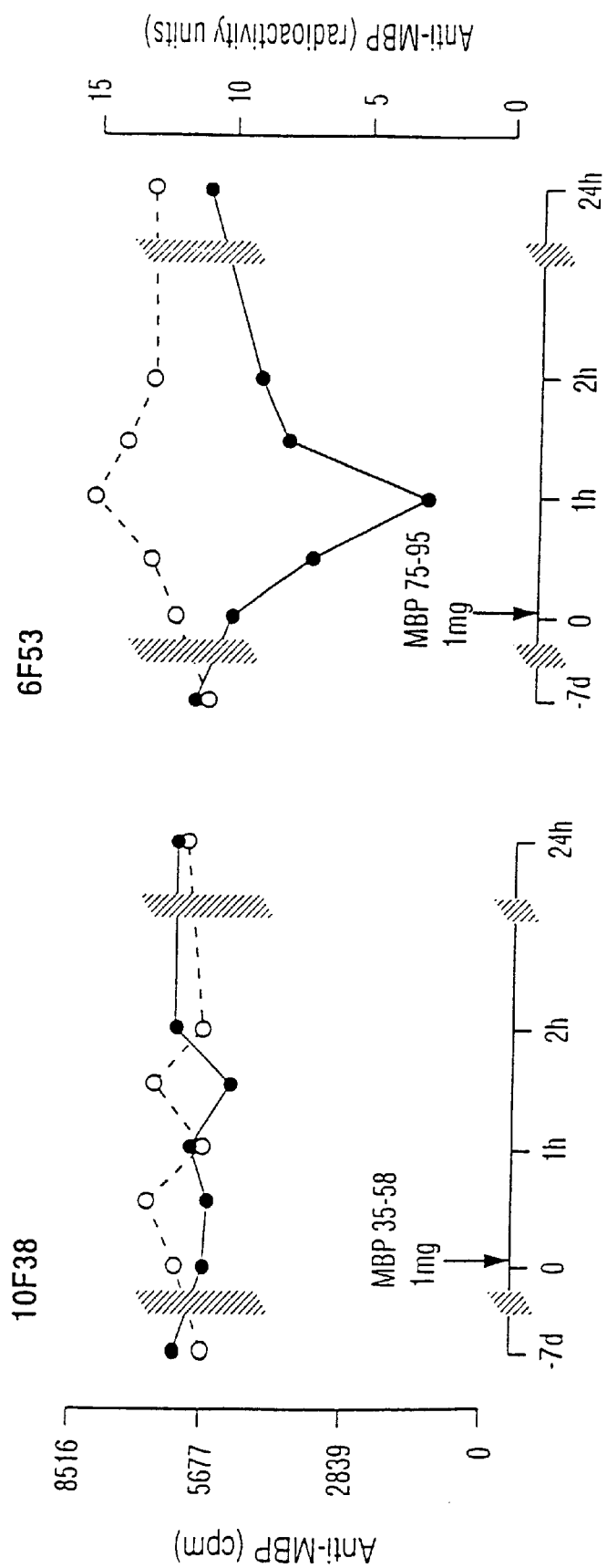
Figure 6C:
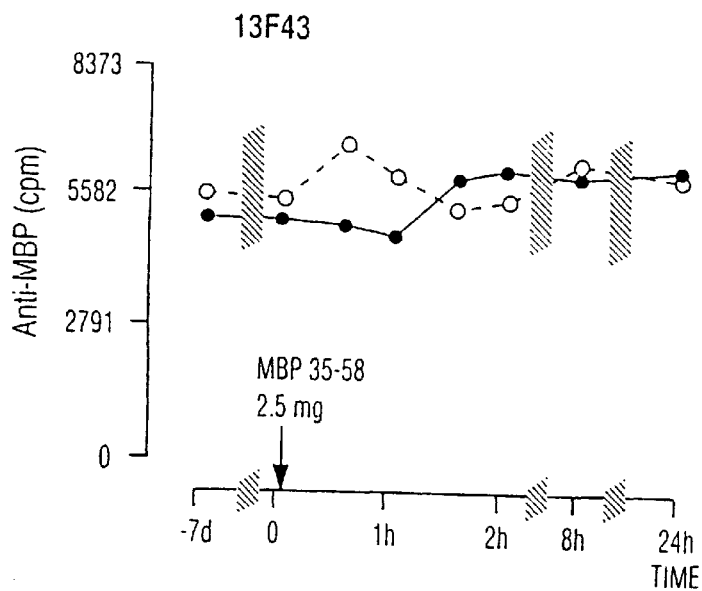
Figure 6D:
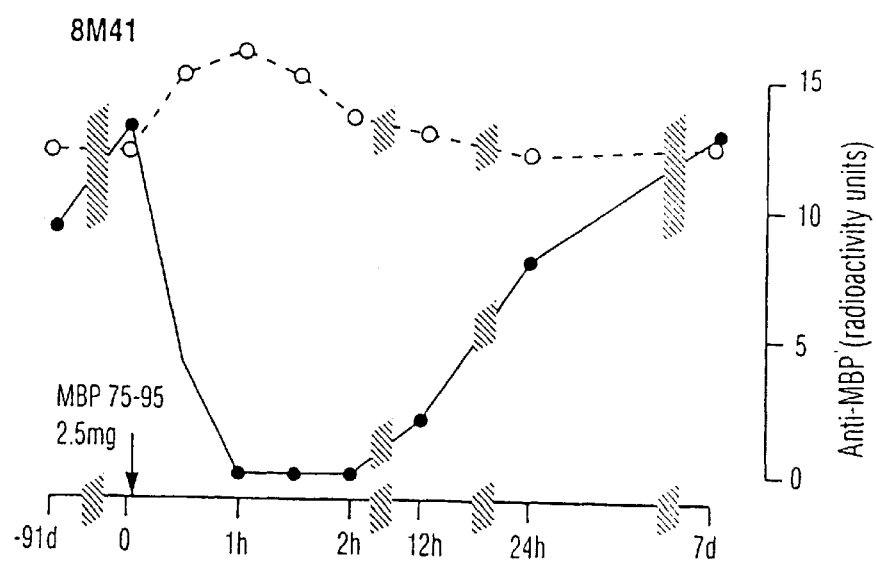
Figure 6E:
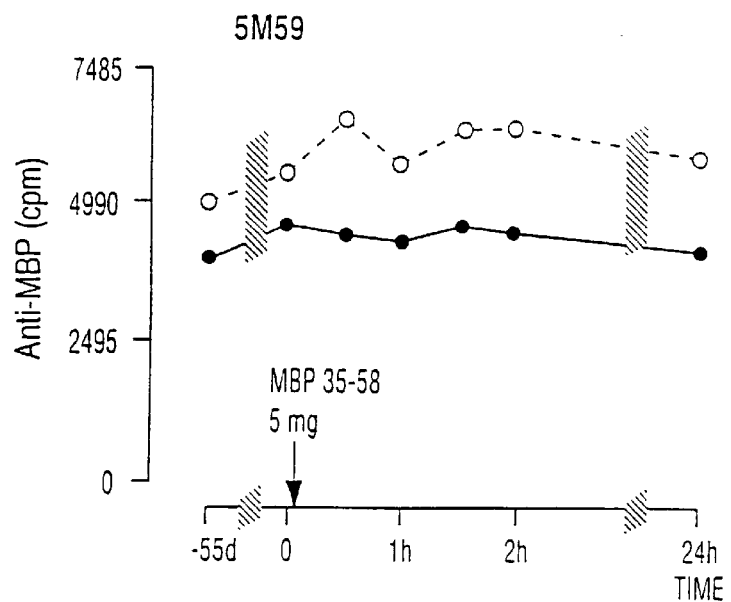
Figure 6F:
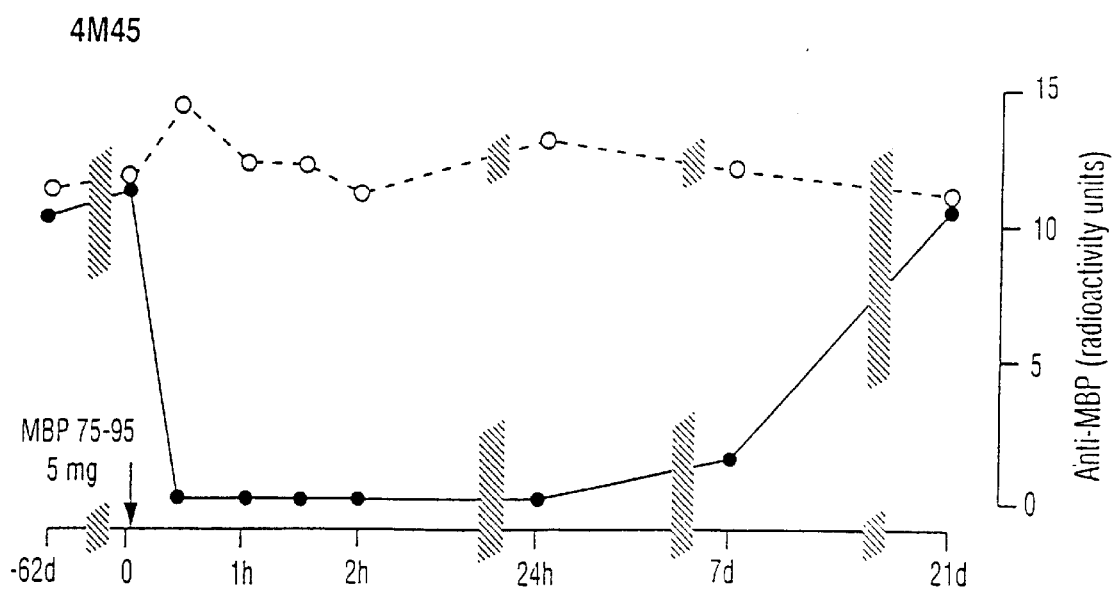
Figure 6G:
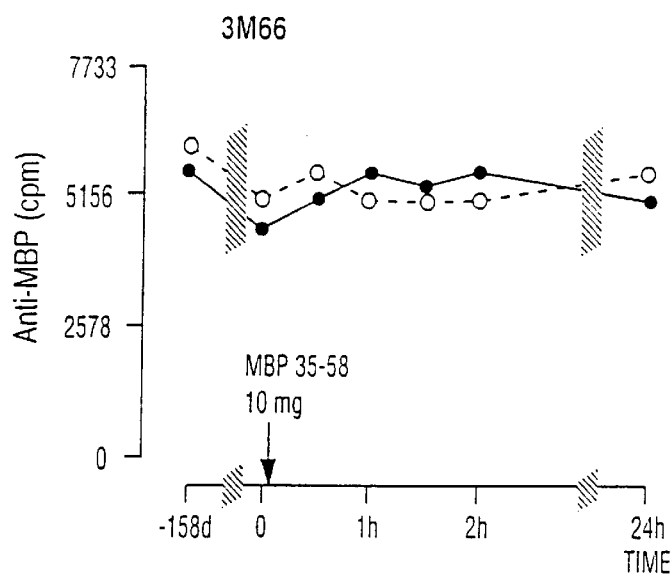
Figure 6H:
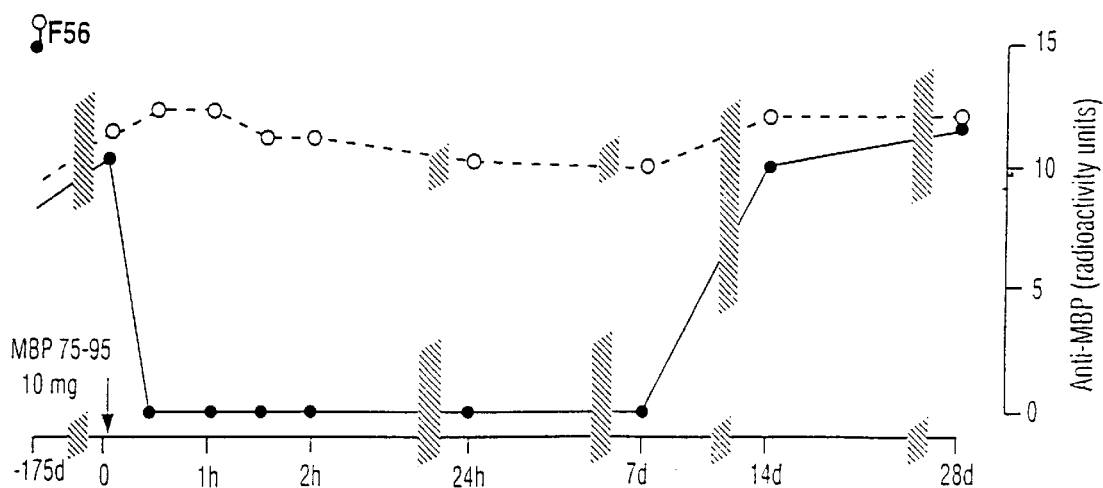

In addition the effect of inoculating 5 cc of normal saline into the CSF was similarly determined in two other patients (4M45 and 5M59; FIGS. 5C and 5D, respectively). These patients served as "time-saline controls". When 5 cc of normal saline were injected intrathecally, F and B anti-MBP levels remained elevated at baseline level when CSF was sampled as above, thus demonstrating that the "dilution effect" on anti-MBP titers was negligible.

Anti-MBP levels were determined by a solid phase radio-immunoassay with human MBP coated on immulon microtiter wells. Immunlon microtiter wells were coated with 100 $\mu$l of 10 $\mu$g/ml of MBP (1 $\mu$g/well) and incubated overnight at 37° C. After quenching with bovine serum albumin (BSA) and three water washes, the wells were stored at room temperature. Samples of 100 $\mu$l of CSF or tissue extracts diluted to 0.010 gm of IgG/L (with 0.01 M PBS, 0.05% Tween 20) were incubated in MBP-coated wells for 1–2 hours at room temperature. After S buffer washes (with 0.01 M PBS, 0.05% Tween 20), wells were incubated with goat anti-rabbit IgG-Fc specific (in 0.01 M PBS, 0.05% Tween 20, 0.5% BSA) for 1 hour at room temperature and then rinsed as above. Finally, $^{125}$I-protein A (or $^{125}$I-protein G) was added and incubated for 1 hour at room temperature. When $^{125}$I-protein G was used as a tracer, ovalbumin replaced BSA in assay buffer and for quenching. After three final water washes, the wells were individually counted. Results are expressed in radioactivity units as follows: (counts of sample−counts of blank)÷(counts of total radioactivity−counts of blank). All samples are run in 10 replicate and counting time is 10 minutes in order to collect >10,000 counts for any positive sample.

Prior to being assayed all CSF and/or tissue samples were diluted to a final IgG concentration of 0.010 g/l. F anti-MBP was detected directly in CSF or tissue extract while B levels of antibody were determined following acid hydrolysis of immune complexes. Non-specific binding was performed for each sample in uncoated wells. For epitope localization, synthetic peptides were firstly reacted with purified antibody in a liquid phase competitive assay and then anti-MBP was determined by radioimmunoassay in all resulting mixtures. Results of the combined competitive binding assay and radioimmunoassay were expressed as percent inhibition of synthetic peptide defined as 100−radioactivity units. Samples were done in 10 replicates and counted for 10 minutes each in a LKB1275 Minigamma counter. A pool of tissue-purified anti-MBP was used at 5 pre-established dilutions as positive controls. Pooled CSF from patients with non-neurological diseases was used as negative controls. Within assay reproducibility was between 3 and 5% and between assay variation was less than 7%.

Persistence of CSF anti-MBP at an elevated and constant level in the control experiments permitted the next step of this research.

Double Blind Peptide Controlled Phase 1 Experiment-Intrathecal Injection

A Phase 1 experiment to determine the effect of synthetic peptide MBP75–95 on F and B titers of CSF anti-MBP was conducted. Subsequent to receiving approval from the Research Ethics Board of the University of Alberta, this project was conducted in patients with clinically definite MS (Schumacher et al., Ann. N.Y. Acad. Sci., 122, 552–568 1965), severely disabled and with advanced progressive disease. After obtaining informed consent, 14 patients volunteered for this study; eight patients were selected on the basis of their initial titer of F CSF anti-MBP (above 8 radioactivity units) (Table 2) to receive one intrathecal injection of either peptide MBP75–95 which bound anti-MBP in vitro or a non-binding control peptide MBP35–58 (Warren and Catz, 1993b). The experiment was conducted in a double blind fashion so that neither the researchers nor the patients had knowledge of the nature of the inoculum. All peptides were coded with 7 digit randomly generated numbers by an independent physician. Paired peptides dissolved in 5 cc normal saline and injected into the CSF by means of a lumbar puncture were administered in increasing dosages of 1, 2.5, 5 and 10 mg. CSF was sampled prior to injection (baseline), at 30 minute intervals for 2 hours after injection, 24 hours later and then at weekly intervals for 3–4 weeks until anti-MBP levels returned to baseline. Cell counts, total protein, glucose, IgG and albumin levels were determined in all CSF samples obtained. F and B anti-MBP levels were determined by radioimmunoassay, as described above.

TABLE 2

| Patient ID #, sex, age | Disease duration (years) | Kurtzke EDSS | CSF anti-MBP (radioactivity units) Free(F) | CSF anti-MBP (radioactivity units) Bound(B) | Selected for research |
| --- | --- | --- | --- | --- | --- |
| 1F56 | 10 | 8.5 - Triplegia | 9 | 10 | Yes |
| 2M50 | 18 | 6 - Paraparesis | 2 | 10 | No |
| 3M66 | 20 | 9 - Quadriplegia | 11 | 12 | Yes |
| 4M45 | 21 | 9 - Quadriplegia | 10 | 11 | Yes |
| 5M59 | 28 | 9 - Quadriplegia | 8 | 10 | Yes |
| 6F53 | 19 | 9 - Quadriplegia | 10 | 9 | Yes |
| 7F33 | 11 | 6 - Paraparesis, ataxia | 5 | 13 | No |
| 8M41 | 8 | 8 - Triplegia | 9 | 12 | Yes |
| 9M49 | 7 | 7 - Paraparesis | 5 | 10 | No |
| 10F38 | 7 | 8.5 - Paraplegia | 11 | 10 | Yes |
| 11M49 | 20 | 8 - Triplegia | 6 | 13 | No |
| 12M35 | 12 | 6.5 - Paraparesis, ataxia | 7 | 12 | No |
| 13F43 | 15 | 8 - Paraplegia | 9 | 10 | Yes |
| 14F32 | 4 | 6 - Paraparesis, ataxia | 8 | 7 | No |

Table 2: Clinical data and CSF anti-MBP levels of 14 patients with chronic progressive MS who volunteered to participate in a Phase 1 research study of one intrathecal injection of MBP synthetic peptides. Since an initially high F anti-MBP (>8 radioactivity units) was necessary in order to achieve a significant post injection change, only 8 of 14 patients were selected for the study.

All peptides used in these studies were synthesized under the "good manufacturing product" (GMP) code using the Fmoc (9 fluorenylmethoxycarbonyl) method by Procyon Inc. (London, Ontario, Canada). Peptide purity was checked by reverse phase high pressure liquid chromatography with a C18 column and water-acetonitrile gradient containing 0.1% TFA. Mass spectroscopy and aminoacid analysis were performed by standard methods. Prior to inoculation all peptides were checked for pyrogenicity (Vancouver General Hospital, Vancouver, Canada), sterility (Provincial Laboratory for Public Health for Northern Alberta, Edmonton, Canada) and acute toxicity (Health Sciences Laboratory Animal Services, University of Alberta, Edmonton, Canada) and they were declared "suitable for administration to humans". Appropriate amounts of coded synthetic peptides were dissolved in 5 cc of sterile normal saline (0.9% sodium chloride injection USP, nonpyrogenic, Baxter Corp, Toronto, Canada), filtered two times through 0.22 m sterilizing filter units (Millex-GX, Millipore Corp., Bedford, Mass., USA) and administered into the CSF by means of a lumbar puncture.

Interpatient Peptide Studies

Patients 6F53, 8M41, 4M45 and 1F56 received synthetic peptide MBP75–95 capable of binding anti-MBP in vitro and patients 10F36, 13F43, 5M59 and 3M66 received a "control", non-binding synthetic peptide MBP35–58 in increasing amounts of 1, 2.5, 5 and 10 mg respectively (FIG. 6). In patient 6F53 (FIG. 6B) who received 1 mg MBP75–95 a 75% decrease of F anti-MBP followed by its immediate return to baseline level was observed; patient 8M41 (FIG. 6D) who received 2.5 mg MBP75–95 showed complete binding-neutralization of F anti-MBP followed by its return to baseline level within 24 hours; in patient 4M45 (FIG. 6F) who received 5 mg MBP75–95, a precipitous and complete F anti-MBP binding-neutralization occurred and persisted for 7 days, having returned to its initial value when sampled 21 days later; patient 1F56 (FIG. 6H) received 10 mg MBP75–95 which also produced complete binding-neutralization of F anti-MBP which persisted for 7 days and had returned to baseline value when sampled 14 and 28 days later. Bound levels of anti-MBP were not significantly altered by one intrathecal inoculation of MBP75–95. In patients 10F38, 13F43, 5M59 and 3M66 who received respectively 1, 2.5, 5 and 10 mg of the "control" non-binding peptide MBP35–58, F and B levels of CSF anti-MBP remained unchanged from initially high baseline levels during the 24 hour experiment (FIGS. 6A, 6C, 6E and 6G, respectively). Traditional CSF parameters of inflammation in MS, such as cell counts, absolute levels of total protein, IgG and albumin, oligoclonal banding, IgG index and CNS IgG synthesis remained unchanged prior to and after peptide administration.

Intrapatient Peptide Studies

Figure 7A:
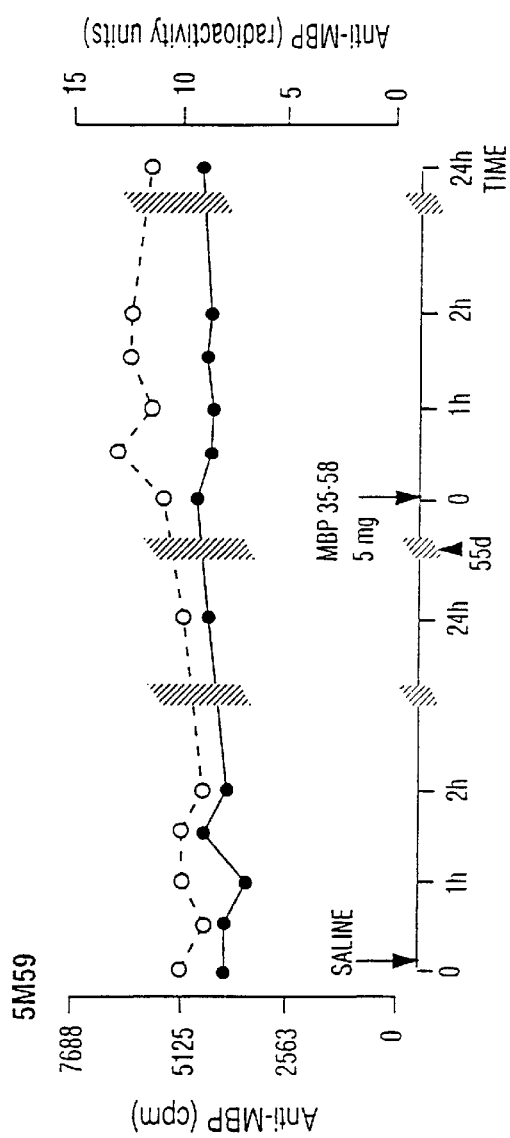
Figure 7B:
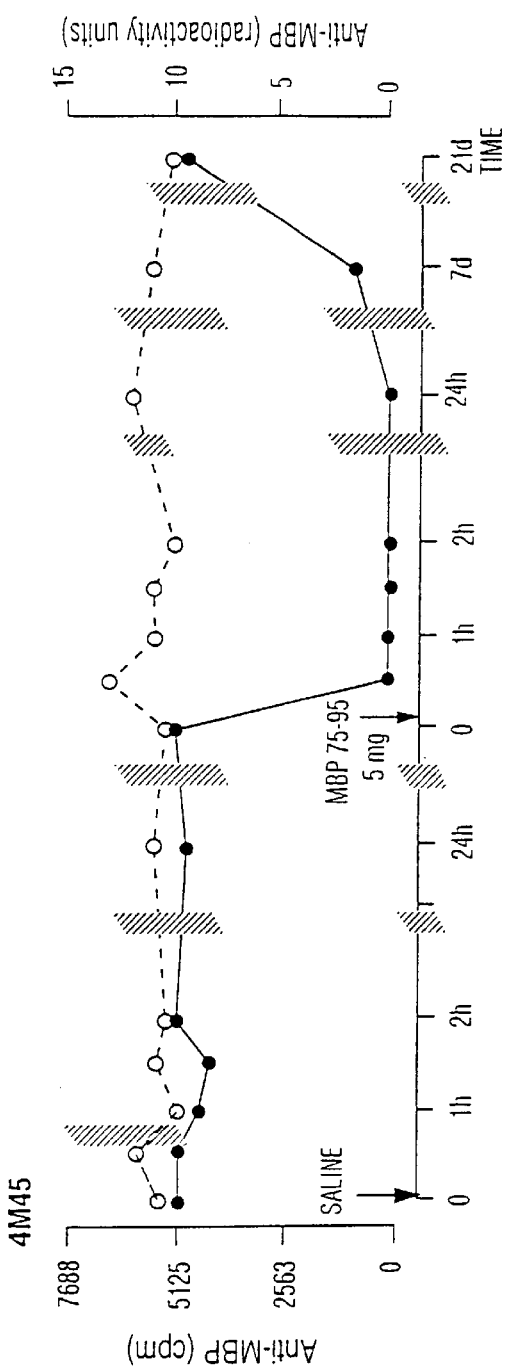
Figure 7C:
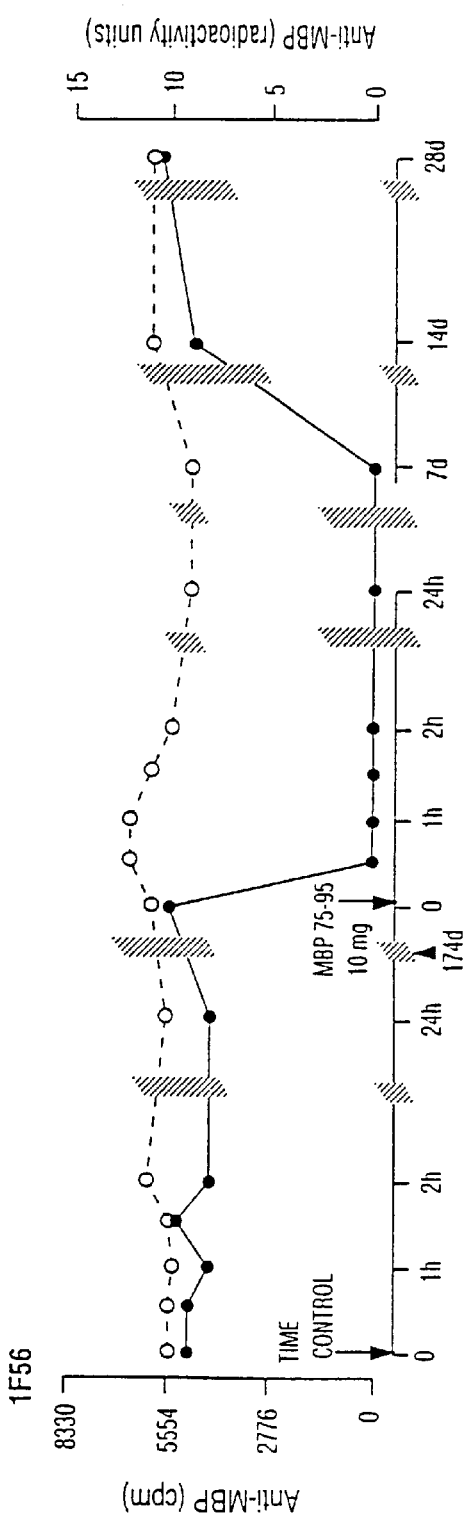
Figure 7D:
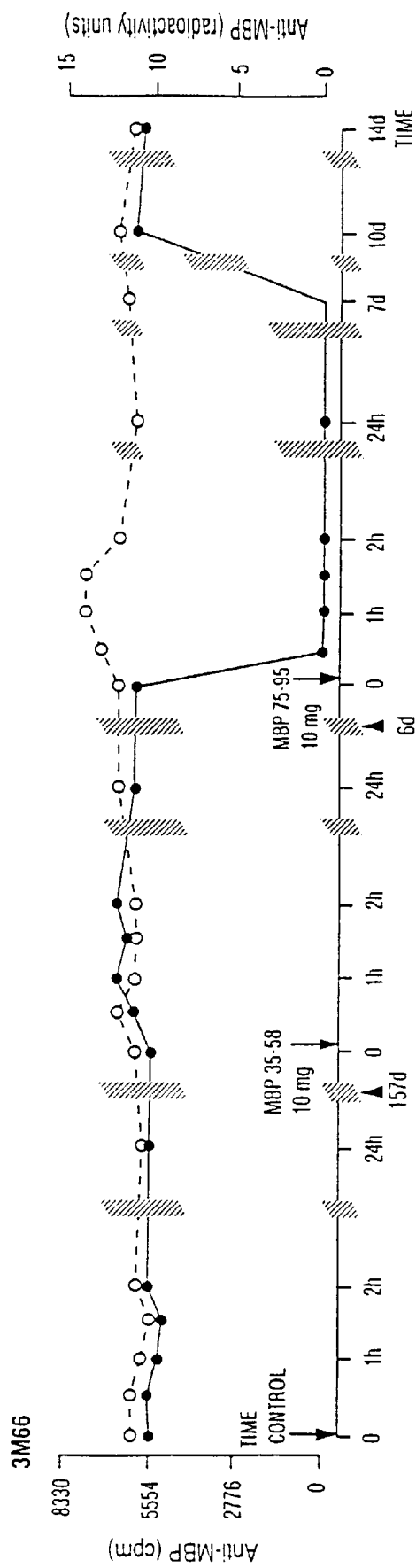

Intrapatient experiments were conducted in order to minimize interpatient variability. In patient 5M59 who was either a "time-saline control" or received 5 mg of the non-binding peptide MBP35–58, F anti-MBP levels remained elevated at baseline level during both experiments (FIG. 7A). Patient 4M45 was initially a "time-saline control" and two months later he received 5 mg MBP75–95. His F anti-MBP remained constantly elevated in all samples collected during the "time-saline" experiment, and it became undetectable after administration of MBP75–95 (FIG. 7B). Similar results were obtained in patient 1F56 who had persistently elevated levels of F antibody during a "time control" experiment and after administration of 10 mg MBP75–95 her F anti-MBP became undetectable (FIG. 7C). A complete study was performed in patient 3M66. His F anti-MBP levels were persistently elevated during a "time control" experiment or when 10 mg MBP35–58 were administered; however, when 10 mg MBP75–95 were injected, F anti-MBP was completely neutralized and remained undetectable for 7 days (FIG. 7D).

Repeated Administration of Synthetic Peptide MBP75–95

After determining that peptide MBP75–95 neutralized F anti-MBP in vivo for periods in excess of 7 days, it was elected to repeatedly inoculate 10 mg MBP75–95 into the spinal fluid at weekly intervals for 10 weeks. This experiment was conducted, in 3 different patients with chronic progressive MS who have not participated in the single peptide injection project and volunteered for this study. F and B anti-MBP were determined 1–2 weeks prior to the first inoculation, prior to and 30 minutes following each of the 10 injections and again 1 and 2 months after the last injection. Cell counts, total protein, glucose, IgG and albumin levels were determined in all CSFs obtained before each of the 10 injections. Prior to the first and after the last injection blood was obtained and analyzed for electrolytes, creatine, cardiac and liver enzymes and hematology panel.

When MS patients with chronic progressive disease received repeated intrathecal injections of 10 mg MBP75–95 at weekly intervals, for periods up to 10 weeks, their initially high F anti-MBP could be rendered undetectable for as long as the peptide was administered; when the peptide was no longer administered, F anti-MBP returned to baseline level within 1–2 months (FIG. 8). Titers of B antibody remained constantly elevated throughout the experiment.

The patients who participated in these studies, who received either a single synthetic peptide injection or repeated weekly injections had chronic progressive multiple sclerosis with an advanced degree of neurological disability. None of these patients reported worsening of their neurological symptoms or MS exacerbations subsequent to intrathecal peptide administration and a cellular response did not develop in CSF. MS patients receiving repeated inoculations of MBP75–95 have been monitored for systemic complications including electrolyte changes as well as cardiac-liver-kidney dysfunction and hematology changes and no adverse complications have occurred.

Intravenous Administration of MBP75–95

Subsequent to determining that intrathecal administration of peptide MBP75–95 produced complete binding-neutralization of F anti-MBP with no change in levels of B antibody, it was decided to determine the effect of intravenous administration of the same peptide on CSF titers of F and B anti-MBP; 500 mg of MBP75–95 were dissolved in 100 cc of normal saline and injected intravenously over 30 minutes into patient 8M41 with CSF anti-MBP monitoring every 30 minutes for the first two hours, 18 hours later as well as 10, 16 and 30 days later. Blood was obtained before injection as well as 16 and 30 days later and analyzed for electrolytes, creatine, cardiac and liver enzymes and hematology panel. Spinal fluid was monitored for cell counts, total protein, glucose, IgG and albumin levels.

As shown in FIG. 8, intravenous administration of 500 mg MBP75–95 did not produce any change in titers of F and B levels of CSF anti-MBP within the first two hours. A 30% decline in CSF F anti-MBP was observed 18 hours later. When CSF was resampled 10, 16 and 30 days later both F and B anti-MBP had declined from their initial level of 11 radioactivity units to 4, 2, and 1 radioactivity units respectively.

A repeated observation in all the patients treated intrathecally was the persistence of elevated levels of bound antibody, while F anti-MBP was undetectable subsequent to intrathecal administration of MBP75–95. This suggested that the inflammatory process which produced auto antibodies to MBP remained active during and subsequent to intrathecal administration of MBP75–95. As a consequence of this observation, MBP75–95 was administered intravenously to a patient who had previously received a single intrathecal injection of the peptide. After intravenous administration both F and B levels of CSF anti-MBP showed a significant decline when monitored for periods up to one month. The decline of F as well as B levels of CSF anti-MBP subsequent to intravenous administration of MBP75–95 implies that there has been downregulation of the autoimmune inflammatory process responsible for the synthesis of anti-MBP.

MBP Epitope for MS Anti-MBP

In order to further localize the MBP epitope for MS anti-MBP, F and B anti-MBP purified by affinity chromatography from CSF and MS brain tissue (Warren, K. G. et al., Ann. Neurol. 35, 280–289, 1994) were reacted in competitive inhibition assays with 41 consecutive MBP synthetic peptides of equal length (each of 10 residues and overlapping the adjacent ones by 9) covering the area between residues 61 and 110 of human MBP. The peptide(s) producing maximum inhibition were considered to be most highly associated with the antibody binding site.

Maximum inhibition ($\geq 80\%$) of purified F and B anti-MBP from MS brain tissue (FIG. 10) was produced by four decapeptides namely MBP84–93, MBP85–94, MBP86–95 and MBP87–96 suggesting that the MBP epitope for MS anti-MBP is located between residues 84 and 96. The minimum area of common amino acid residues is from residue 87 to residue 93. B anti-MBP had a more restricted range than F antibody.

The role of anti-MBP antibodies in the pathogenesis of MS demyelination has not been elucidated and can only be determined by modulating anti-MBP in vivo and subsequently observing the clinical and pathological outcomes.

For example, during an acute relapse of MS, when F/B antibody ratios are above unity a peptide known to bind F anti-MBP could be inoculated intrathecally, in order to bind free circulating antibody and terminate the clinical effects of the acute relapse; weekly administration may be required until remission occurs. In MS patients with chronic progressive disease, intravenous as well as intrathecal peptide administration may be required in order to downregulate the inflammatory mechanisms which produce anti-MBP.

Various modifications may be made to the preferred embodiments without departing from the spirit and scope of the invention as defined in the appended claims.

The embodiments of the invention in which an exclusive property or privilege is claimed are defined as follows:

1. A method of neutralizing anti-myelin basic protein by contacting said anti-myelin protein with a peptide of from about 8 to about 25 amino acids and having a sequence contained within SEQ ID NO:1, including substitutions, additions or deletions thereof, provided that said peptide is capable of neutralizing anti-myelin basic protein, alone or in combination.

2. A pharmaceutical composition containing as an active ingredient a peptide of from about 8 to about 25 amino acids and having a sequence contained within SEQ ID NO:1, including substitutions, additions or deletions thereof, provided that said peptide is capable of neutralizing or modu-

---

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 170 amino acids
      (B) TYPE: amino acid
      (C) STRANDEDNESS: <Unknown>
      (D) TOPOLOGY: linear (ii) MOLECULE TYPE: peptide (vi) ORIGINAL SOURCE:
      (A) ORGANISM: Homo sapiens (vii) IMMEDIATE SOURCE:
      (B) CLONE: human myelin basic protein (xi) SEQUENCE DESCRIPTION: SEQ ID NO: 1:

```
Ala Ser Gln Lys Arg Pro Ser Gln Arg His Gly Ser Lys Tyr Leu Ala
1               5                   10                  15

Thr Ala Ser Thr Met Asp His Ala Arg His Gly Phe Leu Pro Arg His
            20                  25                  30

Arg Asp Thr Gly Ile Leu Asp Ser Ile Gly Arg Phe Phe Gly Gly Asp
        35                  40                  45

Arg Gly Ala Pro Lys Arg Gly Ser Gly Lys Asp Ser His His Pro Ala
    50                  55                  60

Arg Thr Ala His Tyr Gly Ser Leu Pro Gln Lys Ser His Gly Arg Thr
65                  70                  75                  80

Gln Asp Glu Asn Pro Val Val His Phe Phe Lys Asn Ile Val Thr Pro
                85                  90                  95

Arg Thr Pro Pro Pro Ser Gln Gly Lys Gly Arg Gly Leu Ser Leu Ser
            100                 105                 110

Arg Phe Ser Trp Gly Ala Glu Gly Gln Arg Pro Gly Phe Gly Tyr Gly
        115                 120                 125

Gly Arg Ala Ser Asp Tyr Lys Ser Ala His Lys Gly Phe Lys Gly Val
    130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170
``` lating the production of anti-myelin basic protein, alone or in combination.

3. The composition of claim 2, wherein the peptide has a sequence contained within amino acid residues 61–106 of SEQ ID NO:1.

4. The composition of claim 3, wherein the peptide has the formula

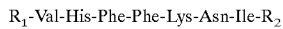

and salts thereof, wherein Val-His-Phe-Phe-Lys-Asn-Ile- is amino acid residues 87–93 of SEQ ID NO:1, wherein $R_1$ and $R_2$ are independently selected from the group consisting of hydrogen, hydroxy, an amino acid residue and a polypeptide residue; provided that $R_1$ and $R_2$ are not both hydrogen or hydroxyl at the same time.

5. The method of claim 1, wherein the peptide has a sequence contained within amino acid residues 61–106 of SEQ ID NO:1.

6. The composition of claim 4, wherein $R_1$ is Asn-Pro-Val- and $R_2$ is hydrogen or hydroxy, the peptide in the claimed composition corresponding to amino acid residues 84–93 of SEO ID NO:1.

7. The composition of claim 4, wherein $R_1$ is Pro-Val- and $R_2$ is -Val, the peptide in the claimed composition corresponding to amino acid residues 85–94 of SEQ ID NO:1.

8. The composition of claim 4, wherein $R_1$ is Val- and $R_2$ is -Val-Thr, the peptide in the claimed composition corresponding to amino acid residues 86–95 of SEQ ID NO:1.

9. The composition of claim 4, wherein $R_1$ is hydrogen or hydroxy and $R_2$ is -Val-Thr-Pro, the peptide in the claimed composition corresponding to amino acid residues 87–96 of SEQ ID NO:1.

10. The composition of claim 4, wherein $R_1$ is Lys-Ser-His-Gly-Arg-Thr-Gln-Asp-Glu-Asn-Pro-Val-(amino acid residues 75–86 of SEQ ID NO:1) and $R_2$ is -Val-Thr, the peptide in the claimed composition corresponding to amino acid residues 75–95 of SEQ ID NO:1.

* * * * *